US011278727B2

(12) United States Patent
Stegemann et al.

(10) Patent No.: US 11,278,727 B2
(45) Date of Patent: Mar. 22, 2022

(54) EFFICIENT DELIVERY OF MULTI-SITE PACING

(71) Applicant: Medtronic, Inc., Minneapolis, MN (US)

(72) Inventors: Berthold Stegemann, Kassel (NL); Richard Cornelussen, Maastricht (NL); Joeri Heynens, Eindhoven (NL); Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 566 days.

(21) Appl. No.: 16/196,732

(22) Filed: Nov. 20, 2018

(65) Prior Publication Data

US 2019/0160288 A1 May 30, 2019

Related U.S. Application Data

(60) Provisional application No. 62/589,906, filed on Nov. 22, 2017.

(51) Int. Cl.
*A61N 1/368* (2006.01)
*A61B 5/363* (2021.01)
(Continued)

(52) U.S. Cl.
CPC .......... *A61N 1/36843* (2017.08); *A61B 5/363* (2021.01); *A61B 5/364* (2021.01);
(Continued)

(58) Field of Classification Search
CPC ............ A61N 1/36843; A61N 1/39622; A61N 1/056; A61N 1/3627; A61N 1/36514;
(Continued)

(56) References Cited

U.S. PATENT DOCUMENTS 6,247,474 B1 6/2001 Greeninger et al.
6,418,346 B1 7/2002 Nelson et al.
(Continued)

FOREIGN PATENT DOCUMENTS

EP 1543864 A1 6/2005
WO 9217240 A1 10/1992

OTHER PUBLICATIONS (PCT/US2018/062256) PCT Notification of Transmittal of the International Search Report and the Written Opinion of the International Searching Authority, dated Feb. 22, 2019, 16 pages.

*Primary Examiner* — Mallika D Fairchild
(74) *Attorney, Agent, or Firm* — Mueting Raasch Group

(57) ABSTRACT

An implantable device and associated method for delivering multi-site pacing therapy is disclosed. The device comprises a set of electrodes including a first and second left ventricular electrodes spatially separated from one another and a right ventricular electrode, all coupled to an implantable pulse generator. The processing circuit coupled to the implantable pulse generator, the processing circuit configured to determine whether a prospective heart failure condition has occurred and if so to trigger the pulse generator to switch from a first pacing mode to a second pacing mode, the first pacing mode comprising delivering only a first pacing pulse to a left ventricle (LV) and thereafter delivering an RV pacing pulse to the right ventricular electrode within a single cardiac cycle and the second pacing mode comprising delivering first and a second pacing pulses to the LV and thereafter delivering an RV pacing pulse to the right ventricular electrode within a single cardiac cycle.

14 Claims, 25 Drawing Sheets

(51) Int. Cl.
  *A61B 5/364* (2021.01)
  *A61N 1/39* (2006.01)
  *A61N 1/05* (2006.01)
  *A61N 1/362* (2006.01)
  *A61N 1/365* (2006.01)
  *A61N 1/37* (2006.01)

(52) U.S. Cl.
  CPC ........... *A61N 1/056* (2013.01); *A61N 1/3627* (2013.01); *A61N 1/3682* (2013.01); *A61N 1/3688* (2013.01); *A61N 1/36514* (2013.01); *A61N 1/39622* (2017.08); *A61N 1/371* (2013.01)

(58) Field of Classification Search
  CPC .... A61N 1/3682; A61N 1/3688; A61N 1/371; A61B 5/364; A61B 5/363
  See application file for complete search history.

(56) References Cited

U.S. PATENT DOCUMENTS

| | | | |
|---|---|---|---|
| 6,442,433 | B1 | 8/2002 | Linberg |
| 6,480,745 | B2 | 11/2002 | Nelson et al. |
| 6,599,250 | B2 | 7/2003 | Webb et al. |
| 6,622,045 | B2 | 9/2003 | Snell et al. |
| 7,027,866 | B2 | 4/2006 | Warkentin |
| 7,555,336 | B2 | 6/2009 | Sheth et al. |
| 7,601,033 | B2 | 10/2009 | Ries et al. |
| 7,654,843 | B2 | 2/2010 | Olson et al. |
| 7,682,316 | B2 | 3/2010 | Anderson et al. |
| 8,078,285 | B2 | 12/2011 | Ganion et al. |
| 8,126,546 | B2 | 2/2012 | Williamson |
| 8,271,072 | B2 | 9/2012 | Houben et al. |
| 8,355,784 | B2 | 1/2013 | Rochat et al. |
| 8,617,082 | B2 | 12/2013 | Zhang et al. |
| 8,750,998 | B1 | 6/2014 | Ghosh et al. |
| 8,777,874 | B2 | 7/2014 | Zhang et al. |
| 8,876,727 | B2 | 11/2014 | Zhang et al. |
| 8,948,869 | B2 | 2/2015 | Ghosh et al. |
| 8,965,507 | B2 | 2/2015 | Mahajan et al. |
| 9,026,208 | B2 | 5/2015 | Morley et al. |
| 9,037,238 | B2 | 5/2015 | Stadler et al. |
| 9,072,914 | B2 | 7/2015 | Greenhut et al. |
| 9,132,274 | B2 | 9/2015 | Ghosh |
| 9,247,883 | B2 | 2/2016 | Sowelam |
| 9,278,219 | B2 | 3/2016 | Ghosh |
| 2003/0083709 | A1 | 5/2003 | Qingsheng et al. |
| 2014/0163633 | A1 | 6/2014 | Ghosh et al. |
| 2015/0142069 | A1 | 5/2015 | Sambelashvili |
| 2016/0228709 | A1* | 8/2016 | Ternes ............... A61N 1/36842 |
| 2016/0271393 | A1* | 9/2016 | Yu ..................... A61N 1/36842 |
| 2018/0126173 | A1* | 5/2018 | Ternes ............... A61N 1/36514 |

\* cited by examiner

CardioSync Optimization - Results

| | Initial Value | Optimized Permanent |
|---|---|---|
| V. Pacing | RV->LV | LV->RV |
| V-V Pace Delay | ≥10 ms | 10 ms |
| Multiple Point LV Delay | ≥10 ms | 10 ms |
| Paced AV... | 150 ms | 160 ms |
| Sensed AV... | 150 ms | 140 ms |

Test Strip | Undo Pending | Print... | ● | PROGRAM | Close

EFFICIENT DELIVERY OF MULTI-SITE PACING

CROSS-REFERENCE TO RELATED APPLICATIONS

The present application claims the benefit of U.S. Provisional Application Ser. No. 62/589,906, filed Nov. 22, 2017, which is incorporated herein by reference in its entirety.

FIELD OF THE DISCLOSURE

The disclosure relates generally to medical devices for delivering electrical stimulation and, in particular, to an apparatus and method for multi-site pacing in the heart.

BACKGROUND

Cardiac resynchronization therapy (CRT) is a treatment for heart failure patients in which one or more heart chambers are electrically stimulated (paced) to restore or improve heart chamber synchrony. CRT therapy involves biventricular pacing which consists of pacing the right ventricle (RV) with a RV electrode and a left ventricle (LV) with a LV electrode or monoventricular pacing which consists of pacing only the left ventricle. Achieving a positive clinical benefit from CRT depends in part on the location of the pacing site, particularly in the left ventricle (LV). Placement of the pacing leads and selecting electrode pacing sites is important in promoting a positive outcome from CRT. Multi-site pacing in a given heart chamber may potentially achieve greater restoration of heart chamber synchrony and therapeutic benefit.

A CRT device can be configured to deliver multisite pacing through a quadripolar lead placed in a coronary sinus branch vein during a single cardiac cycle. However, it is desirable to develop systems and/or methods that efficiently and automatically switch between pacing from a single site to pacing multisite locations within a single cardiac cycle.

BRIEF DESCRIPTION OF THE DRAWINGS

FIG. 5 is a graphical user interface of a computer when determining programmable options related to multi-pacing of cardiac tissue.

SUMMARY OF THE DISCLOSURE

Figure 1:
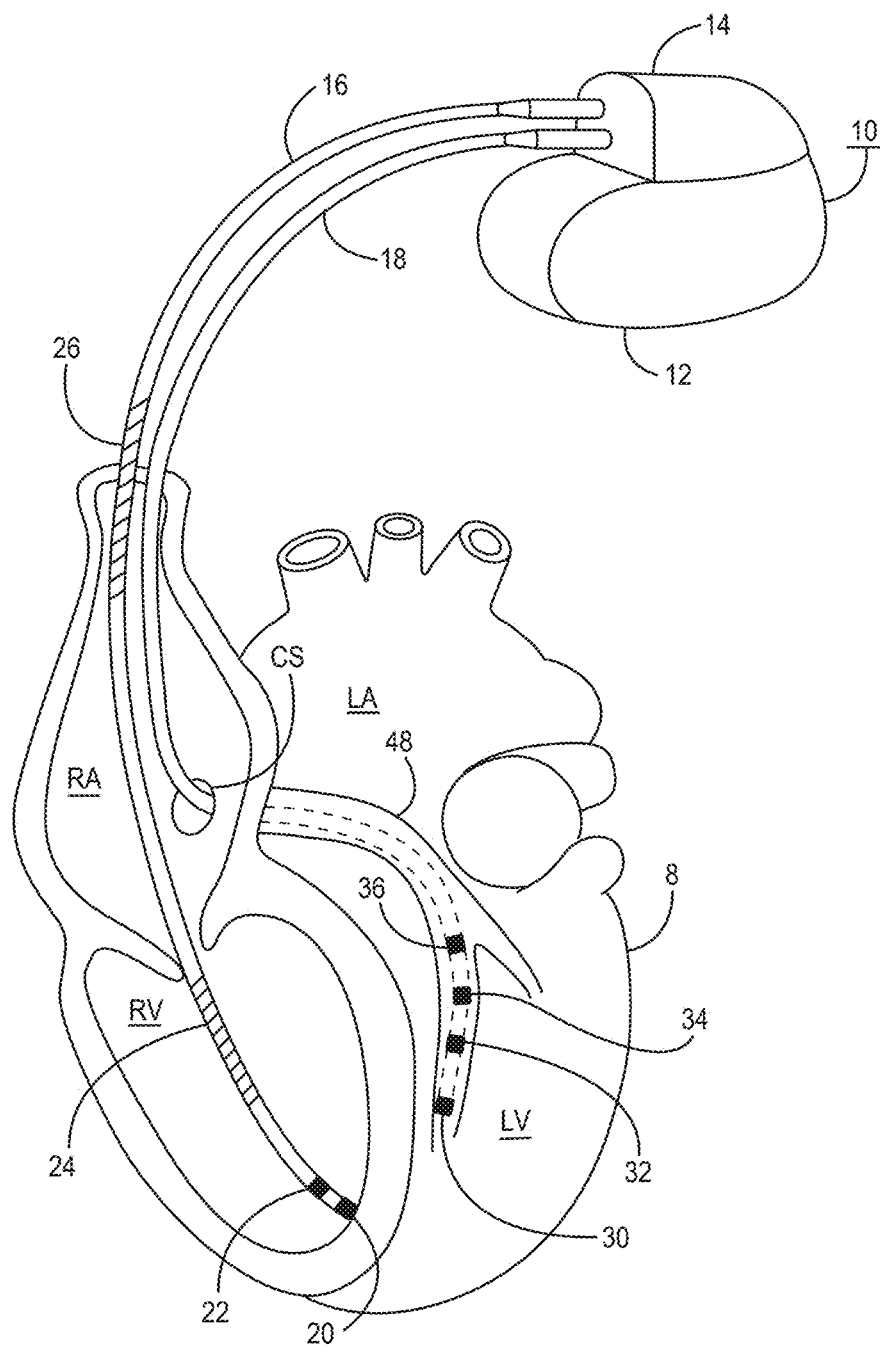
FIG. 1 depicts an implantable medical device (IMD) coupled to a patient's heart.

One or more embodiments are directed to an implantable device and associated method for delivering multi-site pacing therapy is disclosed. The device comprises a set of electrodes including a first and second left ventricular electrodes spatially separated from one another and a right ventricular electrode, all coupled to an implantable pulse generator. The processing circuit coupled to the implantable pulse generator, the processing circuit configured to determine whether a prospective heart failure condition has occurred and if so to trigger the pulse generator to switch from a first pacing mode to a second pacing mode, the first pacing mode comprising delivering only a first pacing pulse to a left ventricle (LV) and thereafter delivering an RV pacing pulse to the right ventricular electrode within a single cardiac cycle and the second pacing mode comprising delivering first and a second pacing pulses to the LV and thereafter delivering an RV pacing pulse to the right ventricular electrode within a single cardiac cycle.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In the following description, a dual-chamber (biventricular) pacing device is described as one illustrative embodiment of a device that may utilize the multi-site pacing methods described herein. This device is used in particular for delivering cardiac resynchronization therapy (CRT) by pacing one or both ventricles. It should be recognized, however, that multi-site pacing may be implemented in numerous device configurations that include at least bipolar pacing capabilities in one or more heart chambers for delivering CRT or any other pacing therapy. Furthermore, aspects of the multi-site electrical stimulation methods may be implemented in any medical device delivering electrical stimulation to excitable body tissue and are not necessarily limited to practice in cardiac pacing applications. CRT can be delivered by one or more leadless pacing devices (e.g. MICRA® commercially available from Medtronic, Inc.) or with leads as shown and described in US 2015-0142069 A1 filed on Mar. 21, 2013, the disclosure of which is incorporated in its entirety herein. Additionally, the CRT therapy can be delivered substernally. In one or more embodiments, the CRT therapy is delivered via a pacing electrode via the coronary sinus. In alternative embodiment, a pacing electrode(s) is positioned inside the left ventricle for multi-site pacing.

FIGS. 17-20 are methods employed by an implantable medical device 10, in a closed loop system, to automatically switch between conventional single site pacing of a cardiac site to multisite pacing. Switching between conventional single site pacing of a cardiac site to multisite pacing may be helpful in achieving capture of cardiac tissue or treatment of the patient.

FIG. 1 depicts a therapy system. The therapy system can comprise implantable medical device (IMD) 10 coupled to a patient's heart 8 by way of a right ventricular (RV) lead 16 and a coronary sinus (CS) lead 18. An exemplary left ventricular lead with a set of spaced apart electrodes is shown in U.S. patent application Ser. No. 13/464,181 filed on May 4, 2012 by Ghosh et al., commonly assigned by the assignee of the present disclosure, the disclosure of which is incorporated by reference in its entirety herein. Exemplary electrodes on leads to form pacing vectors are shown and described in U.S. Pat. Nos. 8,355,784 B2, 8,965,507, 8,126, 546, all of which are incorporated by reference and can Implement features of the disclosure.

The IMD 10 is embodied as a cardiac pacing device provided for restoring ventricular synchrony by delivering pacing pulses to one or both ventricles as needed to control the heart activation sequence. The heart 8 is shown in a partially cut-away view illustrating the upper heart chambers, the right atrium (RA) and left atrium (LA), and the lower heart chambers, the right ventricle (RV) and left ventricle (LV), and the great cardiac vein 48, which branches to form inferior cardiac veins. The great cardiac vein 48 opens into the coronary sinus (CS) in the right atrium.

The transveous leads 16 and 18 connect IMD 10 with the RV and the LV, respectively. It is recognized that in some embodiments, additional leads and/or electrodes may be coupled to an IMD for connecting the IMD with the RA and the LA to provide sensing and/or pacing in three or all four chambers of the heart.

Each lead 16 and 18 carries pace/sense electrodes coupled to insulated, elongated conductors extending through leads 16 and 18. A remote indifferent housing electrode 12 is formed as part of the outer surface of the housing of the IMD 10. The pace/sense electrodes and the remote indifferent housing electrode 12 can be selectively employed to provide a number of pace/sense electrode combinations for pacing and sensing functions. The electrodes can be configured to be "canodes," which are electrodes configured to serve as cathodes or anodes depending upon the selected path of the electrode.

RV lead 16 is shown as a transveous, endocardial lead passed through the RA into the RV. The RV lead 16 is formed with a proximal lead connector adapted for insertion into a connector bore of IMD connector block 14. Examples of connector modules may be seen with respect to U.S. Pat. No. 7,601,033 issued Oct. 13, 2009, U.S. Pat. No. 7,654,843 issued Feb. 2, 2010, and assigned to the assignee of the present invention, the disclosure of which are incorporated by reference in their entirety herein. Connector module 14, as illustrated, takes the form of an IS-4 quadrapolar connector, but any appropriate connector mechanism may be substituted. The lead connector (not shown in FIG. 1) electrically couples electrodes 20, 22, 24, and 26 carried by RV lead 16 to internal circuitry of IMD 10 via connector block 14. RV pace/sense tip electrode 20 and proximal RV pace/sense ring electrode 22 are provided for RV pacing and sensing of RV EGM signals. RV lead 16 additionally carries an RV coil electrode 24 and a superior vena cava (SVC) coil electrode 26, which may be used for delivering high-voltage cardioversion or defibrillation shocks. RV ring electrode 22, RV coil electrode 24 or SVC coil electrode 26 are used in some embodiments as an anode paired with an electrode positioned along the LV for delivering unipolar pacing pulses in the LV during anodal capture analysis.

In the illustrative embodiment, a multi-polar LV CS lead 18 is passed through the RA, into the CS and further into a cardiac vein 48 to extend the distal four pace/sense electrodes 30, 32, 34 and 36 along the LV chamber to achieve LV pacing and sensing of LV EGM signals using any combination of electrodes 30 through 36. The LV CS lead 18 is coupled at a proximal end lead connector (not shown) inserted into a bore of IMD connector block 14 to provide electrical coupling of electrodes 30 through 36 to IMD internal circuitry. In other embodiments, the multi-polar lead 18 may include more than four electrodes or fewer than four electrodes. Any medical electrical lead configured to deliver multi-site pacing pulses to tissue can be employed to implement the methods described herein. An exemplary medical electrical lead can be the ATTAIN PERFORMA® LV lead, commercially available from Medtronic, PLC. located in Ireland. The lead can be used to implement method 200 to deliver pacing pulses at the same time or about the same time from two or more electrodes (e.g. LV1, LV2, LV3, LV4, LV5, LV6, LV7, LV8 . . . LVn where n is an integer designated by the lead manufacturer).

In addition to or alternative embodiments, pace/sense electrodes may be operatively positioned along the LV for pacing the LV myocardium using multiple LV leads advanced into different cardiac veins, using endocardial leads and electrodes, epicardial leads and electrodes, or any combination thereof. As used herein, delivering electrical stimuli that causes the ventricle to respond is commonly referred to as capturing a ventricle. Additionally, pacing a heart chamber using an electrode positioned "along a heart chamber" refers to pacing the myocardial tissue of the heart chamber to capture (i.e. evoke a response to the pacing pulse) that heart chamber, and includes using electrodes operatively positioned at endocardial, epicardial, or intravenous locations or any combination thereof. To pace epicardial tissue, an epicardial lead could be used. In one or more embodiments, a leadless pacemaker device can be used for pacing, such as that which is described in U.S. patent application Ser. No. 14/178,711 filed on Feb. 12, 2014, entitled SYSTEMS AND METHODS FOR LEADLESS PACING AND SHOCK THERAPY, incorporated by reference in its entirety.

The depicted positions of the leads and electrodes shown in FIG. 1 in or about the right and left ventricles are approximate and merely illustrative. It is recognized that alternative leads and pace/sense electrodes that are adapted for placement at pacing or sensing sites on or in or relative to the RA, LA, RV and/or LV may be used in conjunction with the methods described herein. For example, in a three chamber pacing device, a RA lead may be positioned carrying a tip and ring electrode for pacing and sensing in the right atrial chamber. Additionally, in a four chamber embodiment, LV CS lead 22 could bear proximal LA CS pace/sense electrode(s) positioned along the lead body to lie adjacent the LA for use in pacing the LA or sensing LA EGM signals. A multi-chamber device in which methods described herein may be implemented is generally disclosed in U.S. Pat. No. 7,555,336 to Sheth, et al., hereby incorporated herein by reference in its entirety.

The electrodes designated above as "pace/sense" electrodes can generally be used for both pacing and sensing functions. "Pace/sense" electrodes can be selected to be used exclusively as pace or sense electrodes or to be used for both pacing and sensing in programmed combinations for sensing cardiac signals and delivering cardiac stimulation pulses along selected sensing and pacing vectors. A pacing vector includes a pair of electrodes that comprise one or more cathodes and one or more anodes. Typically, the cathode delivers the charge into cardiac tissue since energy typically flows from the cathode into the anode; however, the polarity can be switched to cause the anode to deliver the charge to the tissue. Separate or shared indifferent pace and sense electrodes can also be designated in pacing and sensing functions, including the use of RV coil electrode 24 and/or SVC coil electrode 26 as a pacing anode or used for sensing cardiac signals.

Figure 2:
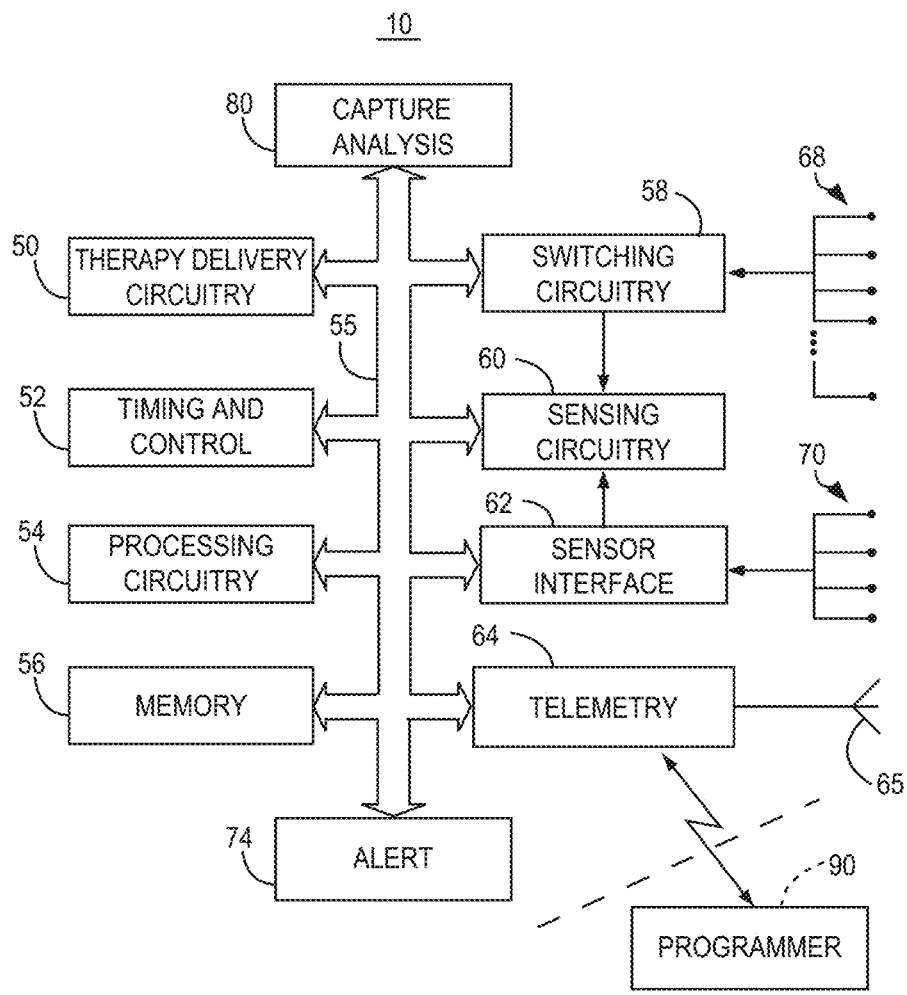
FIG. 2 is a functional block diagram of the IMD shown in FIG. 1.
Figure 3A:
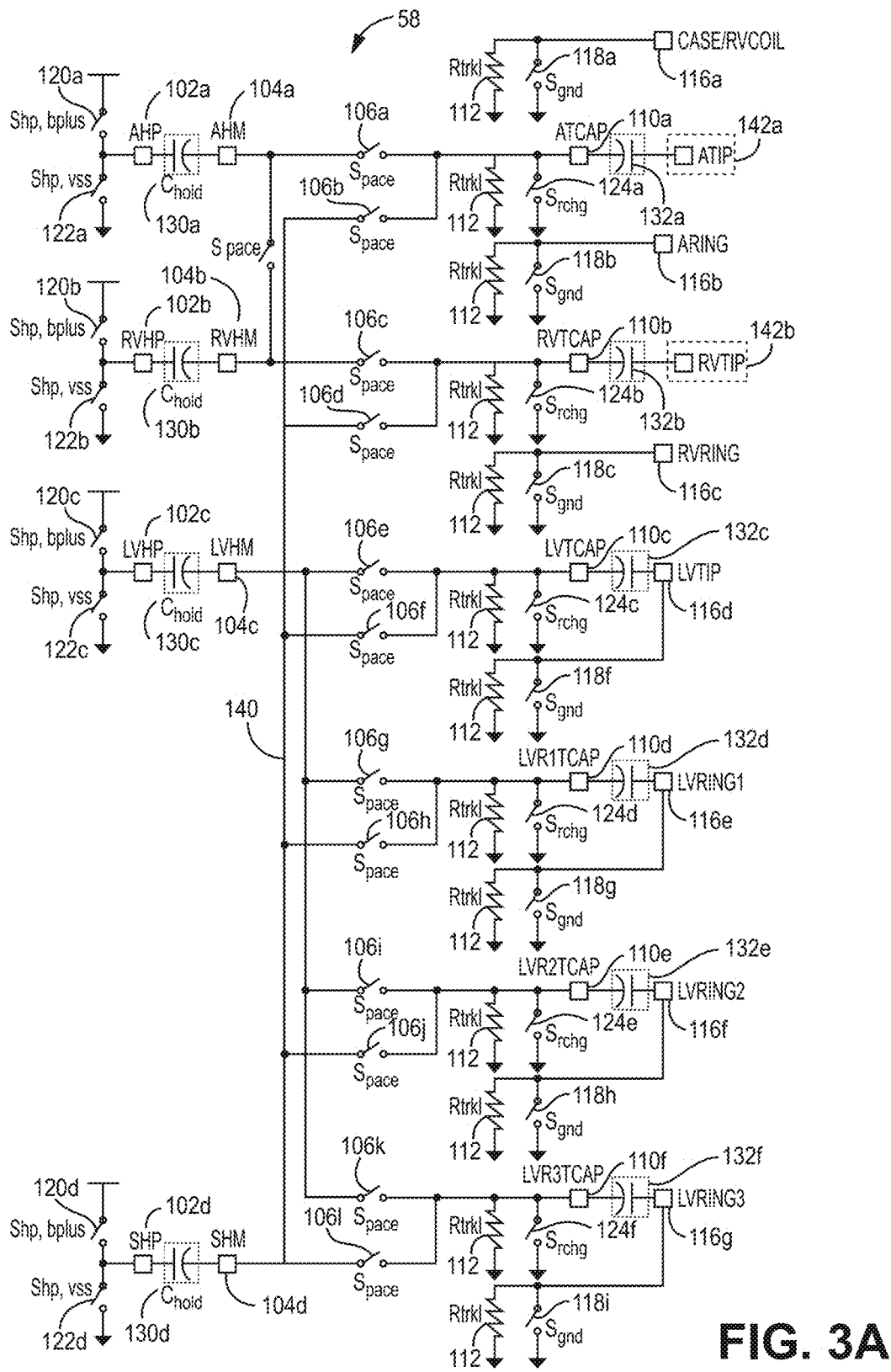
FIG. 3A is a schematic circuit diagram of a switching matrix for delivering multi-site pacing.
Figure 3B:
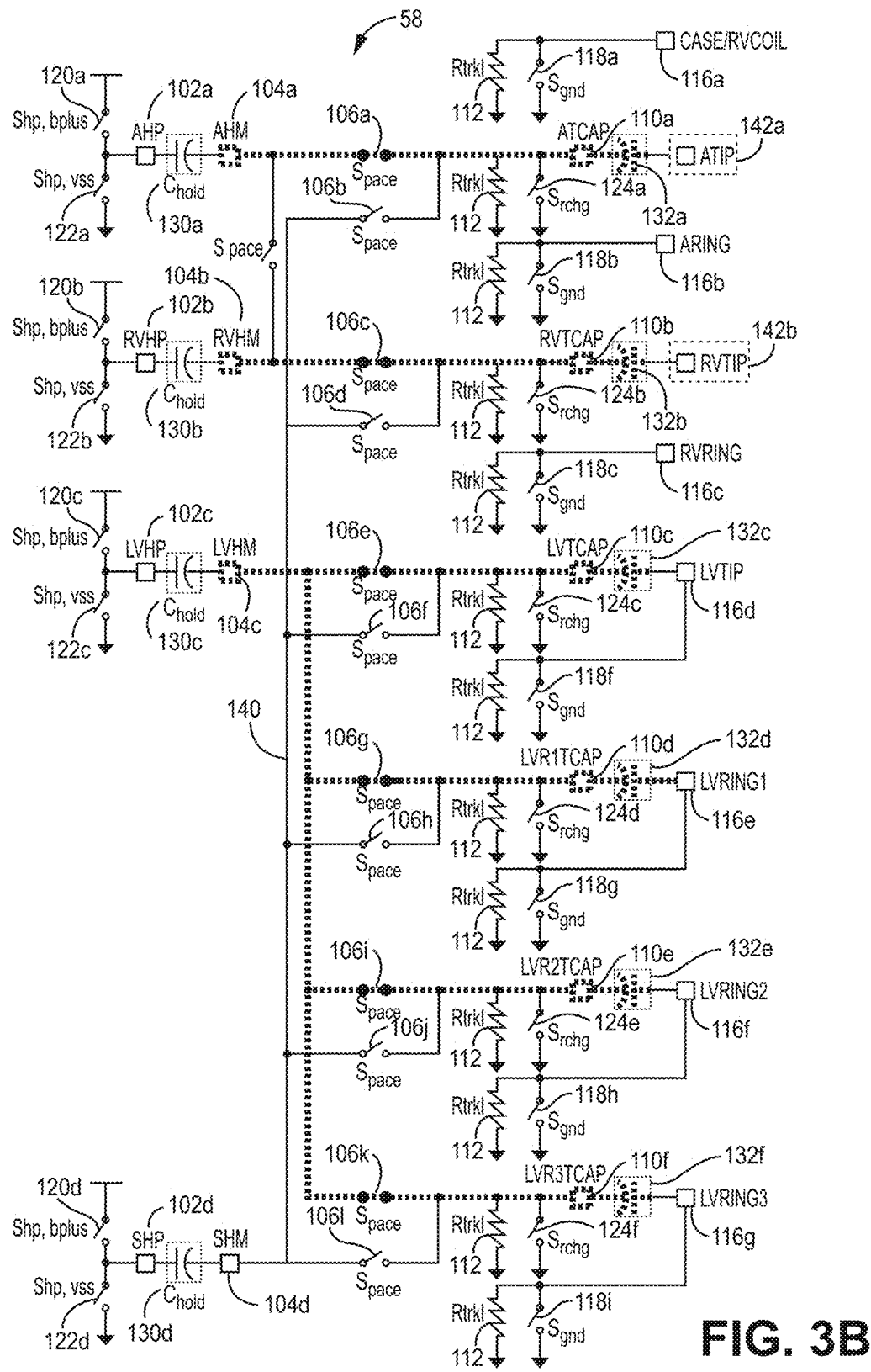
FIG. 3B is a schematic circuit diagram of a switching matrix that selects a path requiring an electrode to serve as a cathode.
Figure 3C:
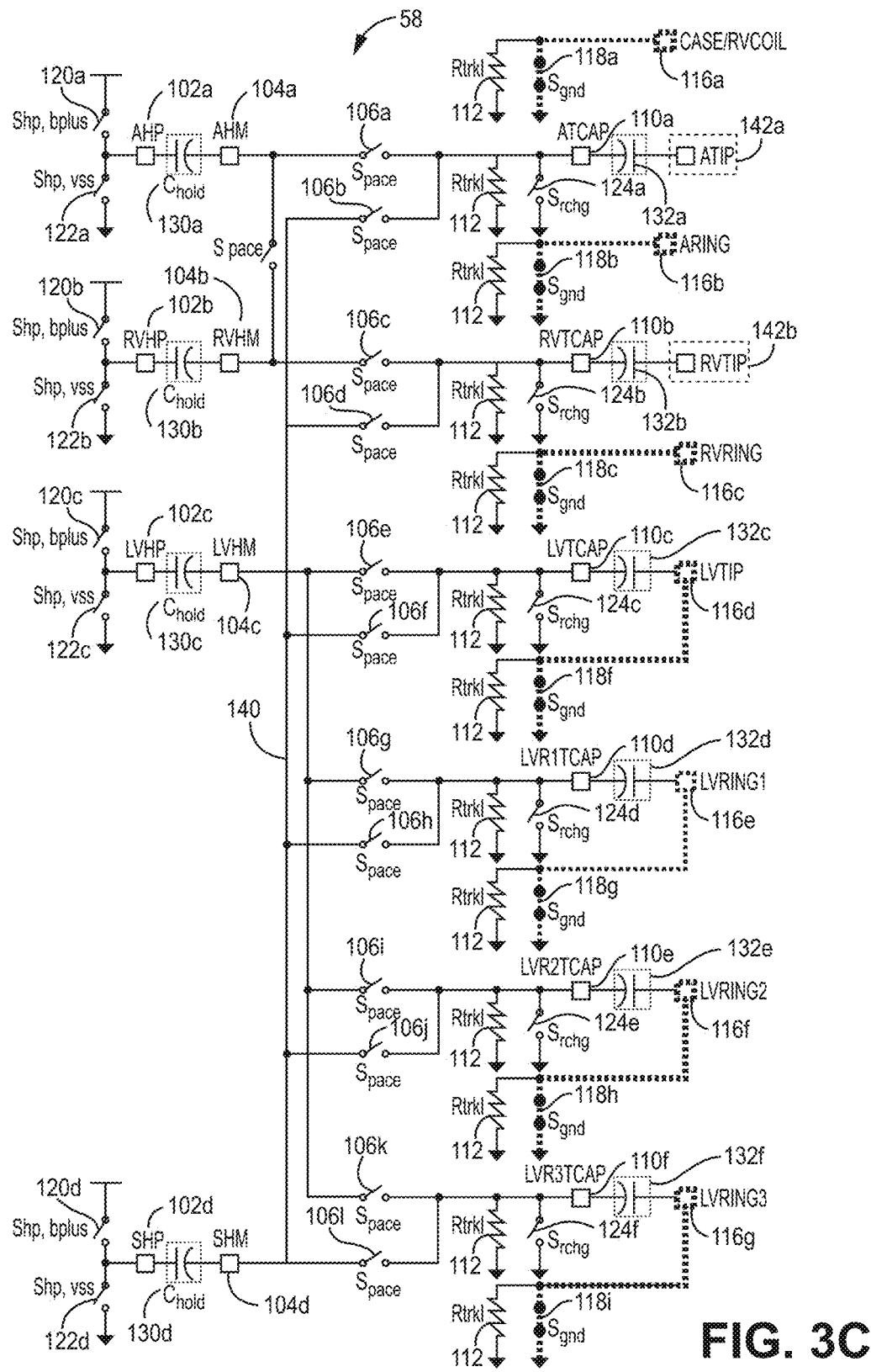
FIG. 3C is a schematic circuit diagram of a switching matrix that selects a path requiring an electrode to serve as an anode.

FIG. 2 is a functional block diagram of IMD 10. IMD 10 generally includes timing and control circuitry 52 and an operating system that may employ processing circuitry 54 for controlling sensing and therapy delivery functions in accordance with a programmed operating mode. For example, timing and control circuitry 52 can signal switching matrix 58 (also referred to as switching circuit) to perform a number of actions. To illustrate, timing and control circuitry 52 can signal switching matrix 58 to cause the switches to trigger the output capacitor to discharge a pacing pulse to its associated electrode. Details of pacing are shown in FIGS. 3A-3C and described below with respect to switch matrix 58.

The switching matrix 58 can be configured to automatically switch from delivering pacing pulses to a single LV electrode to a first and second LV electrodes when a triggering condition is detected by the processing circuit 54. Exemplary triggering conditions can include detection of a patients' worsening HF condition, ventricular arrhythmia, ICD pos-shock condition. In one or more other embodiments, a triggering condition may involve processor circuit 54 determining that a heart failure event (i.e. heart failure hospitalization, heart attack, etc.) can occur within thirty days.

In another example, a signal from timing and control 52 can cause the switches to allow the coupling capacitor to recharge. Processor 54 and associated memory 56 are coupled to the various components of IMD 10 via a data/address bus 55. Processor 54, memory 56, timing and control 52, and capture analysis module 80 may operate cooperatively as a controller for executing and controlling various functions of IMD 10.

Processing circuitry 54 may include any one or more of a microprocessor, a controller, a digital state machine, a digital signal processor (DSP), an application specific integrated circuit (ASIC), a field-programmable gate array (FPGA), or equivalent discrete or integrated logic circuitry. In some examples, processor 54 may include multiple components, such as any combination of one or more microprocessors, one or more controllers, one or more DSPs, one or more ASICs, or one or more FPGAs, as well as other discrete or integrated logic circuitry. The functions attributed to processor 54 herein may be embodied as software, firmware, hardware or any combination thereof. In one example, capture analysis module 80 and/or sensing module 60 may, at least in part, be stored or encoded as instructions in memory 56 that are executed by processor 54.

A therapy system can further comprise processing circuitry 54 configured to identify one or more features of a cardiac contraction within the signal, determine whether the cardiac contraction is a fusion beat based on the one or more features, and control a timing interval for delivery of the ventricular pacing based on the determination.

Another example is a method for delivering cardiac resynchronization therapy by a pacing device. The method comprising, by processing circuitry of a medical device system comprising the pacing device receiving a signal from a sensor of the pacing device, the signal indicating mechanical activity of a heart, identifying one or more features of a cardiac contraction within the signal, determining whether the cardiac contraction is a fusion beat based on the one or more features, and controlling a timing interval for delivery of ventricular pacing by the pacing device based on the determination.

IMD 10 includes therapy delivery module 50 for delivering a therapy in response to determining a need for therapy based on sensed physiological signals. Therapy delivery module 50 includes a signal generator, or stimulation generator or implantable pulse generator, for providing electrical stimulation therapies, such as cardiac pacing or arrhythmia therapies, including cardiac resynchronization therapy. Cardiac pacing involves delivering electrical pacing pulses to the patient's heart, e.g., to maintain the patient's heart beat (e.g., to regulate a patient's heart beat, to improve and/or maintain a patient's hemodynamic efficiency, etc.). Cardiac pacing can involve delivering electrical pacing pulses ranging from about 0.25 volts to about 8 volts and more preferably, between 2-3 volts. Therapies are delivered by module 50 under the control of timing and control module 52. Therapy delivery module 50 is coupled to two or more electrodes 68 via a switch matrix 58 for delivering pacing pulses to the heart. Switch matrix 58 may be used for selecting which electrodes and corresponding polarities are used for delivering electrical stimulation pulses. Electrodes 68 may correspond to the electrodes 12, 20, 22, 24, 26, 30, 32, 34, and 36 shown in FIG. 1 or any electrodes coupled to IMD 10.

Timing and control 52, in cooperation with processor 54 and capture analysis module 80, control the delivery of pacing pulses and/or recharge signals by therapy delivery module 50 according to a programmed therapy protocol, which includes the option of selecting multi-site pacing at sites along a heart chamber using methods described herein. Selection of multiple pacing sites and control of the pacing therapy delivered may be based on results of activation time measurements or an anodal capture analysis algorithm or a combination of both, an example of which may be seen with respect to U.S. patent application Ser. No. 13/301,084 filed on Nov. 21, 2011 by Demmer et al., commonly assigned by the assignee of the present disclosure, the disclosure of which is incorporated by reference in its entirety herein.

For example, the detection of anodal capture may be used to select which of electrodes 30 through 36 and corresponding polarities are used in delivering a cardiac pacing therapy. As such, capture analysis module 80 is configured to determine pacing capture thresholds and detect the presence of anodal capture for determining both anodal and cathodal capture thresholds for a given pacing vector in some embodiments.

Electrodes 68 are also used for receiving cardiac electrical signals. Cardiac electrical signals may be monitored for use in diagnosing or monitoring a patient condition or may be used for determining when a therapy is needed and in controlling the timing and delivery of the therapy. When used for sensing, electrodes 68 are coupled to sensing module 60 via switch matrix 58. Sensing module 60 includes sense amplifiers and may include other signal conditioning circuitry and an analog-to-digital converter. Cardiac EGM signals (either analog sensed event signals or digitized signals or both) may then be used by processor 54 for detecting physiological events, such as detecting and discriminating cardiac arrhythmias, determining activation patterns of the patient's heart, measuring myocardial conduction time intervals, and in performing anodal capture analysis and pacing capture threshold measurements as will be further described herein. IMD 10 may additionally be coupled to one or more physiological sensors 70. Physiological sensors 70 may include pressure sensors, accelerometers, flow sensors, blood chemistry sensors, activity sensors, heart sound sensors, or other physiological sensors for use with implantable devices. Exemplary heart sound sensors for a subcutaneous device are shown, described and positioned in the body in U.S. Pat. No. 7,682,316 to Anderson et al. The subcutaneous heart sound sensor could be placed along with a second sensor on a lead behind the lungs. Heart sound sensor implementation in ICD's and/or CRT devices is exemplarily described, shown and positioned in a patient's body in U.S. Pat. No. 8,078,285 B2 to Ganion et al. Other exemplary heart sound sensors are shown, described and positioned in the body in U.S. Pat. Nos. 8,876,727, 8,617,082 and 8,777,874, all of which are incorporated by reference in their entirety.

Physiological sensors may be carried by leads extending from IMD 10 or incorporated in or on the IMD housing. Sensor interface 62 receives signals from sensors 70 and provides sensor signals to sensing module 60. In other embodiments, wireless sensors may be implanted remotely from IMD 10 and communicate wirelessly with IMD 10. IMD telemetry circuitry 64 may receive sensed signals transmitted from wireless sensors. Sensor signals are used by processor 54 for detecting physiological events or conditions. In addition, processor circuitry 54 is configured to determine whether a triggering condition is present. A triggering condition can relate to switching from conventional CRT (i.e. monoventricular pacing, biventricular pacing) to multiple point pacing (i.e. delivery of a first pacing pulse to the LV and a second pacing pulse to a different tissue location on the LV, all of which is performed during a single cardiac cycle. Sensor input can be used to determine which pacing configuration (i.e. biventricular pacing, fusion pacing (e.g. left ventricular (LV)-only pacing, triventricular pacing (TriV) or dual LV pacing) and/or AV/VV timing are most suitable for a patient. Heart sound sensor data can be used to determine intensity of 51, V sense to 51 interval, peak to peak amplitude or combination of the above. The heart sound sensor can be located in or on the housing of the IMD (also referred to as the ("Can") impedance sensed for contractility is between the electrodes within the system such as intracardiac, from one of the electrodes back to the Can. Exemplary configurations that may implement features herein are shown in U.S. Pat. No. 9,026,208 to Morely, et al., U.S. Pat. No. 8,078,285 to Ganion et al., U.S. Pat. No. 6,247,474 B1 to Greenineger et al. and U.S. Pat. No. 8,617,082 B2 to Zhang et al, commonly assigned by the assignee of the present disclosure, the disclosures of which are incorporated by reference in their entirety herein.

The operating system includes associated memory 56 for storing a variety of programmed-in operating mode and parameter values that are used by processor 54. The memory 56 may also be used for storing data compiled from sensed signals and/or relating to device operating history for telemetry out upon receipt of a retrieval or interrogation instruction. The processor 54 in cooperation with therapy delivery module 50, sensing module 60 and memory 56 executes an algorithm for measuring activation times for selecting pacing sites for delivering multi-site pacing. Processor 54 is configured to select a first anode and a first cathode to form a first pacing vector. Processor 54 then selects a second anode and a second cathode to form a second pacing vector. Additional anode and cathode pairs may also be selected by processor 54.

A capture analysis algorithm may be stored in memory 56 and executed by processor 54 and/or capture analysis module 80 with input received from electrodes 68 for detecting anodal capture and for measuring pacing capture thresholds.

Microprocessor 54 may respond to capture analysis data by altering electrode selection for delivering a cardiac pacing therapy. Data relating to capture analysis may be stored in memory 56 for retrieval and review by a clinician and that information may be used in programming a pacing therapy in IMD 10.

IMD 10 further includes telemetry circuitry 64 and antenna 65. Programming commands or data are transmitted during uplink or downlink telemetry between IMD telemetry circuitry 64 and external telemetry circuitry included in programmer 90.

Programmer 90 may be a handheld device or a microprocessor based home monitor or bedside programming device used by a clinician, nurse, technician or other user. IMD 10 and programmer 90 communicate via wireless communication. Examples of communication techniques may include low frequency or radiofrequency (RF) telemetry using Bluetooth or MICS but other techniques may also be used.

A user, such as a physician, technician, or other clinician, may interact with programmer 90 to communicate with IMD 10. For example, the user may interact with programmer 90 to retrieve physiological or diagnostic information from IMD 10. Programmer 90 may receive data from IMD 10 for use in electrode selection for CRT, particularly data regarding cathodal and anodal capture thresholds and other measurements used in electrode selection such as hemodynamic measurements and LV activation times.

A user may also interact with programmer 90 to program IMD 10, e.g., select values for operational parameters of the IMD. For example, a user interacting with programmer 90 may select programmable parameters controlling a cardiac rhythm management therapy delivered to the patient's heart 8 via any of electrodes 68. Exemplary programmable pacing parameters include atrioventricular delay (AV delay), left ventricle to right ventricle delay (VV or V-V delay), pacing amplitude, pacing rate, pulse duration, and pacing pathway or vector (e.g., bipolar such as a lead tip electrode to a lead ring electrode, etc. or unipolar such as a lead tip electrode to IMD casing, or housing), which all may be configured to ensure effective therapy to the patient. AV delay which may generally be described as a programmable value representing a time period between atrial electrical activity, whether intrinsic (e.g., natural) or paced, and the delivery of ventricular pacing. The optimal value of the AV delay has generally been defined as a delay that produces the maximum stroke volume for a fixed heart rate or the maximum cardiac output for a sinus node driven heart rate. Exemplary A-V delay, shown in FIG. 5, is a nominal 150 or 160 ms.

Processor 54, or a processor included in programmer 90, is configured to compute battery expenditure estimates in some embodiments. Using measured pacing capture thresholds and lead impedance measurements, along with other measured or estimated parameters, the predicted battery longevity of the IMD 10 may be computed for different pacing configurations. This information may be used in selecting or recommending a multi-site pacing configuration. As such, IMD 10 is configured to perform lead impedance measurements and determine other parameters required for estimated energy expenditure calculations, which may include but are not limited to a history of pacing frequency, capture thresholds, lead impedances, and remaining battery life.

Further, the IMD 10 may be operable to use various electrode configurations to deliver pacing therapy, which may be unipolar, bipolar, quadripolar, or further multipolar. For example, a multipolar lead may include several electrodes that can be used for delivering pacing therapy. Hence, a multipolar lead system may provide, or offer, multiple electrical vectors to pace from. A pacing vector comprises a cathode and an anode. The cathode may be at least one electrode located on a lead while the anode may be an electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector. While not shown explicitly in FIG. 2, it is contemplated that a user may interact with programmer 90 remotely via a communications network by sending and receiving interrogation and programming commands via the communications network. Programmer 90 may be coupled to a communications network to enable a clinician using a computer to access data received by programmer 90 from IMD 10 and to transfer programming instructions to IMD 10 via programmer 90. Reference is made to commonly-assigned U.S. Pat. No. 6,599,250 (Webb et al.), U.S. Pat. No. 6,442,433 (Linberg et al.) U.S. Pat. No. 6,622,045 (Snell et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, hereby incorporated herein by reference in their entirety.

Switch matrix 58, shown in greater detail in FIGS. 3A-3C, provides increased configurations over the prior art. For example, a greater number of pacing configurations are attainable due to the ability to select whether an electrode serves as a cathode (FIG. 3B) or an anode (FIG. 3C). Additionally, or alternatively, the increased pacing configurations can perform sequential pacing along the LV electrodes in a single cardiac cycle by generating a sequence of pacing commands from the timing and control circuitry 52 to the respective output capacitors $C_{hold}$. Moreover, the pacing path may be changed "pace to pace" or preloaded depending on the hardware configuration. For example, an electrode could serve as a cathode during one pace and switch to an anode on the next pace based upon instructions executed by the processor. An example of this switching function would occur based on LV capture thresholds from an anode/cathode combination in relation to the myocardium. Stimulation from a cathode typically has low threshold than anode stimulation. Determining the best electrode based on minimal capture threshold requires switching electrodes from anodes to cathodes. Also, in an LV sequence a anode of the first pace could be configured as a cathode of the second pace, if the first pace/rechange sequence was completed.

In addition to providing increased pacing configuration options, switch matrix 58 provides more efficient and effective passive recharging configurations. Passive recharging (also referred to as repolarization) involves a recharging current that travels in the opposite direction of the pacing current. The passive recharging current serves to balance the total charge at a coupling capacitor. A net charge of zero at the coupling capacitor prevents corrosion from occurring at the electrode.

Switch matrix 58 is depicted as including a support or safety pacing path 140, output capacitors ($C_{hold}$) 130a-d, trickle charge resistors ($R_{trkl}$) 112a, tip coupling capacitor ($C_{tip}$) 132a-f, pacing switches ($S_{pace}$) 106a-l, ground switches pace, ($S_{gnd}$) 118a-118i, passive recharging switches ($S_{rchg}$) 124a-f, terminal to the integrated circuit connecting to a capacitor (TCAP) 110a-f, electrodes 116a-116g, and sets of pads HP 102a-d along the integrated circuit that are used to connect to an external device. Output capacitors $C_{hold}$ 130a-c, $C_{tip}$ 124a-f, ATIP 142a and RVTIP 142b are externally located to switch matrix 58, as indicated by the dashed lines in FIGS. 3A-3C. Support or safety pacing path 140 is used for capture management. Lack of capture causes safety pacing to be triggered to ensure that subsequent pacing pulses result in capture. For example, safety pacing may increase the amplitude of the pacing signal to ensure capture of cardiac tissue occurs. Safety pacing switches include $S_{pace}$ 106b, 106d, 106f, 106h, 106j and 106l.

The switch matrix 58 allows pacing pulses to be delivered through one or more pacing vectors within the same cardiac cycle. A pacing vector includes one or more cathodes (FIG. 3B) directly referenced to one or more anodes (FIG. 3C). The selected path to the anode or cathode can be automatically controlled by the processor accessing one or more data registers (i.e. data storage area in memory) or inputted by a user through a user interface on the programmer. The anode and the cathode can be selected by enabling the respective controls in the registers (not shown) to implement simultaneous or substantially simultaneous pacing.

As shown in FIG. 3B, cathodes include atrial terminal capacitor (ATCAP) 110a and $C_{tip}$, right ventricular terminal capacitor (RVTCAP) 110b and $C_{tip}$, left ventricular terminal capacitor (LVTCAP) 110c, left ventricular ring 1 terminal capacitor (LVR1TCAP) 110d and $C_{tip}$, left ventricular ring electrode 2, terminal capacitor (LVR2TCAP) 110e and $C_{tip}$, left ventricular ring electrode 3 terminal capacitor (LVR3TCAP) 110f and $C_{tip}$ Anodes comprise a case (also referred to as a housing or a can) or right ventricular coil (case/RV coil) 116a, atrial ring (ARING) 116b, left ventricular tip electrode (LVTIP (shown as electrode 30 in FIG. 1)) 116d, left ventricular ring electrode 32 (LVRING1) 116e, left ventricular ring electrode 2 (LVRING2 (shown as electrode 34 in FIG. 1)) 116f, and left ventricular ring electrode 3 (LVRING3 (shown as electrode 36 in FIG. 1)) 116g.

Each pacing vector includes a pacing path and a recharging or repolarization path. In order to better understand the pacing and passive recharge paths, a portion of the switching matrix 58 related to the pacing vector formed by the atrial tip electrode (i.e. cathode shown in FIG. 3B) and the atrial ring electrode (i.e. anode shown in FIG. 3C) is depicted in greater detail in FIGS. 12A-12C. The pacing path and recharging path shown, pace to pace (i.e. escape interval), in FIGS. 12A-12C exemplify the various pacing vectors shown in FIGS. 3A-3C.

Figure 12A:
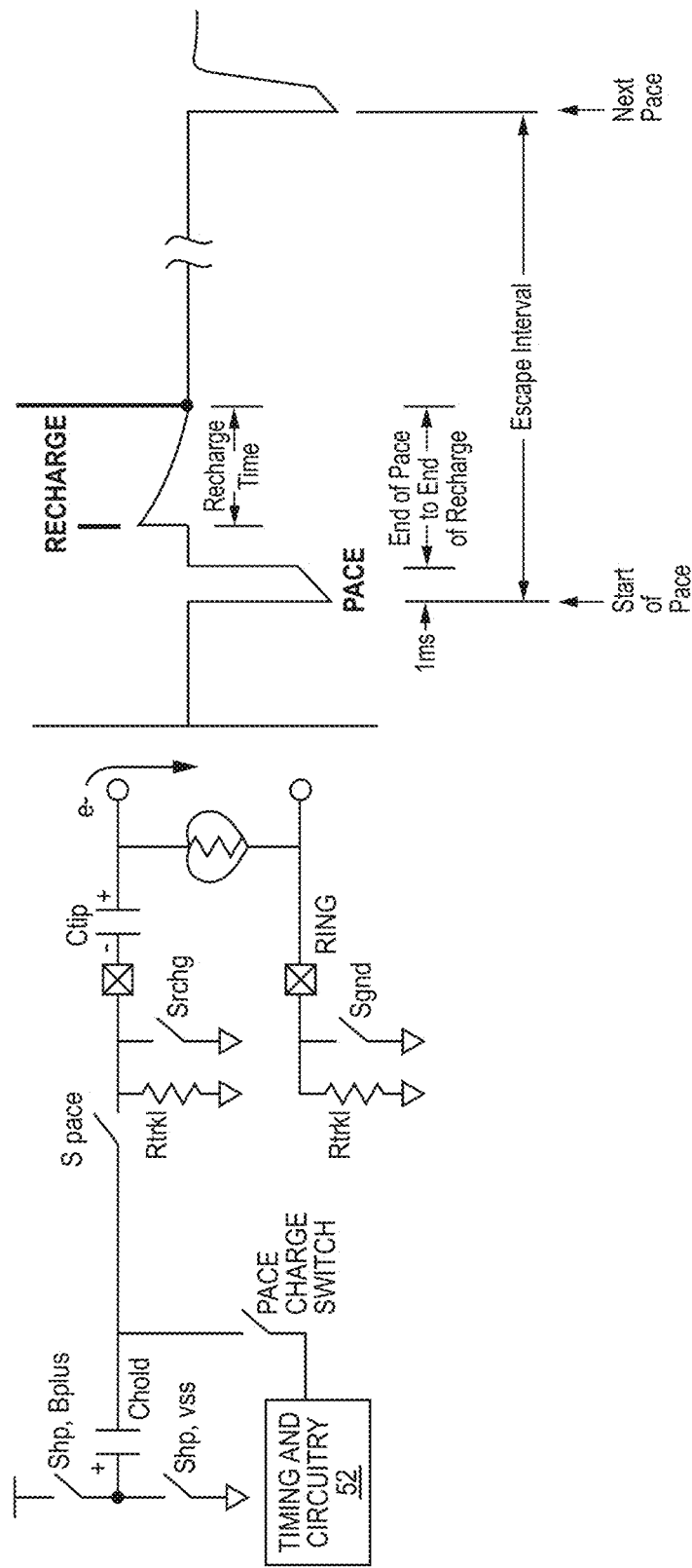
FIG. 12A depicts a simplified view of a portion of the switching matrix from FIGS. 3A-3C.
Figure 12B:
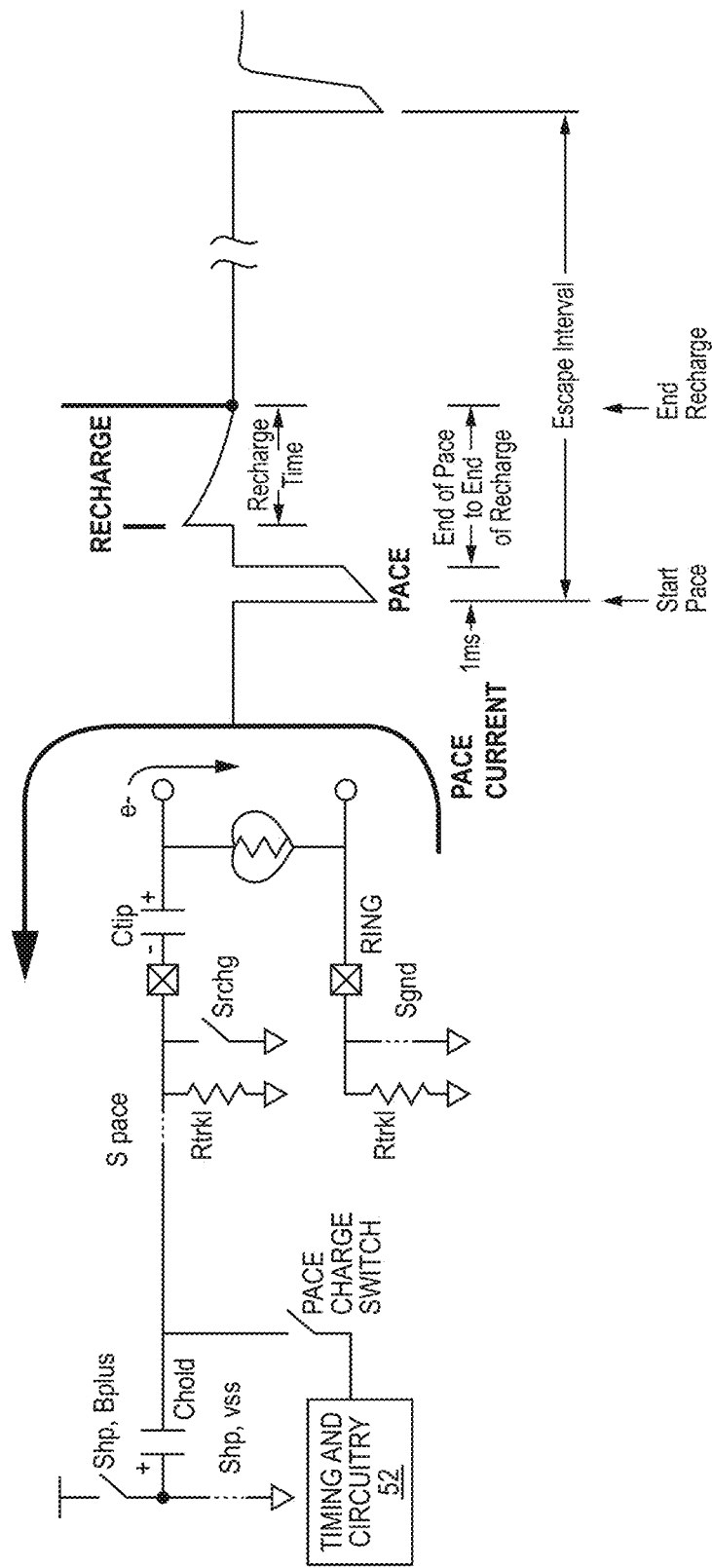
FIG. 12B depicts the switches that are either open or closed in the switching matrix of FIG. 12A when a pacing pulse is being delivered.
Figure 12C:
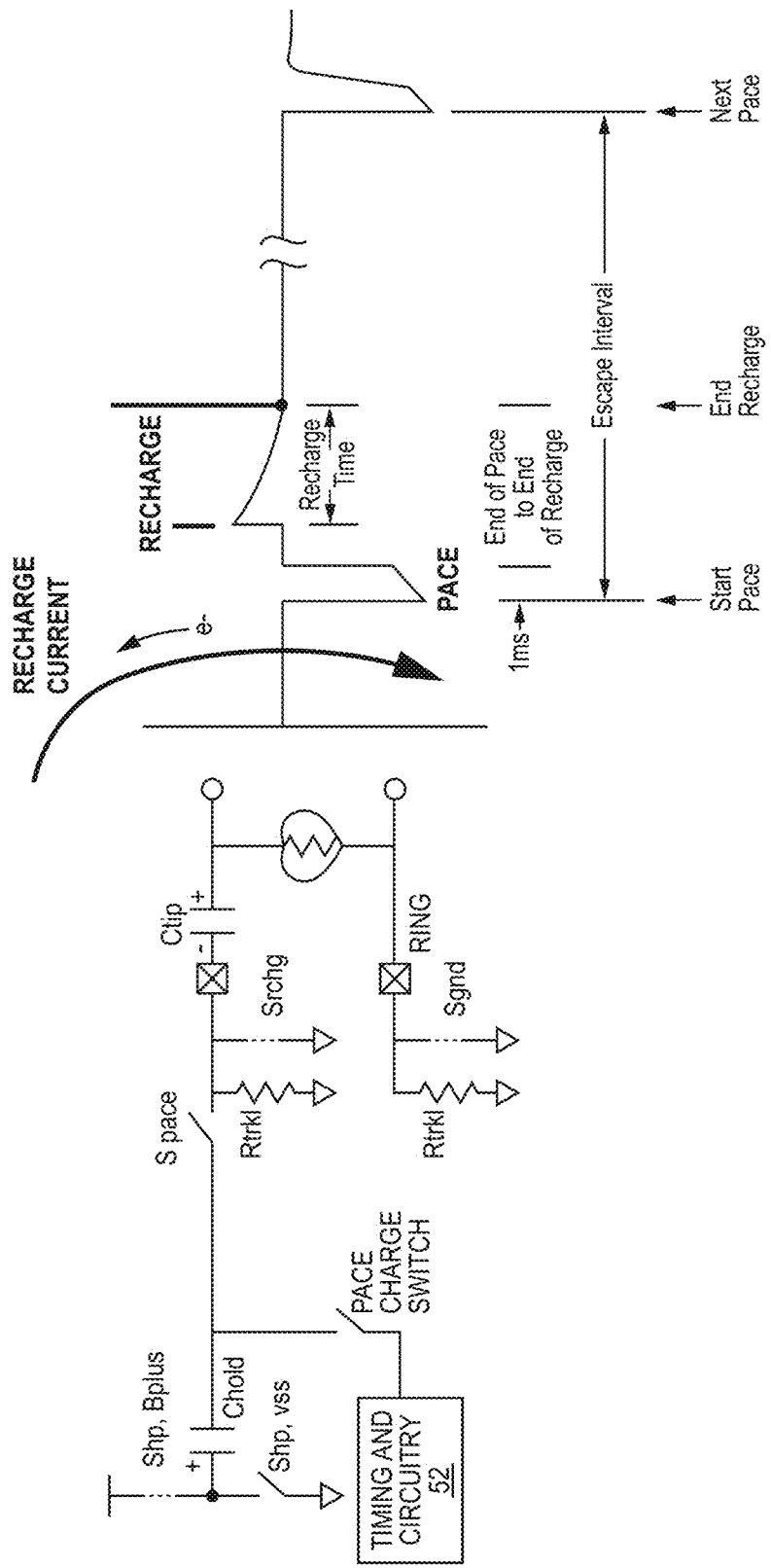
FIG. 12C depicts the switches that are either open or closed in the switching matrix of FIG. 12A when passive recharge occurs.

Referring to FIG. 12A, a circuit diagram is shown relative to an exemplary escape interval which is a pace-to-pace time diagram. Before a digital pacing signal is sent to switching matrix 58, the output capacitor Chou is connected to the power source (e.g. battery) by closed battery positive terminal switch ($S_{BPLUS}$) so that output capacitor $C_{hold}$ can be charged until the desired voltage (e.g. 8 volts or less, 7 volts or less, 6 volts or less, 5 volts or less etc.) is attained in order to deliver the next pacing pulse. After timing and control circuitry 52 generates a digital pace signal that starts at time equal to zero and extends for a certain amount of time (e.g. about 1 ms), switches $S_{hp,vss}$ and $S_{gnd}$ are closed, as shown in FIG. 12B. The output capacitor $C_{hold}$ is connected to the tip coupling capacitor ($C_{tip}$) 132 via closed switch $S_{pace}$. Tip coupling capacitor $C_{tip}$, with its positive and negative plates shown in FIGS. 12A-12C, is external to switching matrix 58 and is configured to prevent DC voltage from passing through the heart. Once switches $S_{hp,vss}$, $S_{pace}$, $S_{gnd}$ are closed, the pacing pulse current flows between the ring/case electrode (i.e. anode) and the tip electrode (i.e. cathode).

In the particular example shown in FIG. 12B, the pace current travels, by convention, in the direction in which positive charge would move, as denoted in FIG. 12B i.e. from the atrial ring electrode to the atrial tip electrode. The actual flow of electrons (e⁻) is in the opposite direction of the pace current. Due to the current direction, the ring/case electrode is positively charged with respect to the paced tip electrode. Charge, and therefore voltage, is accumulated on the tip coupling capacitor, $C_{tip}$. Accumulation of charge on the coupling capacitor $C_{tip}$ is undesired to maintain charge neutrality.

Referring to FIG. 12C, to remove the charge on tip coupling capacitor $C_{tip}$, a passive recharge signal is generated to balance the total charge to a net zero charge. Timing and control circuitry 52 signals switching matrix 58 to perform passive recharge. A set of switching sequences are implemented for passive recharge or repolarization to occur. For example, the $S_{pace}$ switch is opened which creates an open circuit between $C_{hold}$ and the electrodes thereby stopping the pacing operation. Thereafter, switches $S_{gnd}$ or $S_{hp}$ are opened. This switching sequence keeps the ring or case electrodes connected to a circuit reference (i.e. VSS) until after the output capacitor $C_{hold}$ voltage is disconnected from the tip and ring electrodes via the $S_{pace}$ switch being open.

Switch $S_{rchg}$ closes which causes the tip capacitor $C_{tip}$ (i.e. cathode) used in the prior pacing operation to then be connected to reference voltage VSS. After the tip capacitor $C_{tip}$ is connected to negative supply voltage VSS, the desired ring or case electrode is reconnected to supply voltage VSS by closing switch $S_{gnd}$ shown in FIG. 12C. Once both switches are closed, the recharge current path is completed through the external load. Current flow for the recharge path is the opposite direction of the pace current. The flow of electrons e⁻ flows in the opposite direction of the recharge current. In the present example, the recharge current flows from tip electrode to the ring/case electrode. Based on the current direction, the "recharged" tip electrode is positive with respect to the "recharged" electrode (e.g. ring/case electrode). The recharge time is typically about 6.8 ms or about 7 ms; however, recharge time can be greater (e.g. up to 20 ms) or lower (e.g. less than 7 ms). After the recharge current is generated, the total net charge at the coupling capacitor is now zero charge or about zero charge.

To ensure the net charge is zero or about zero volts at the coupling capacitor, the recharge time period is either set or adjustable. Automatically setting the recharge time period can be implemented by the hardware or computer instructions. For example, each hardware time register associated with each recharge time period for a coupling capacitor can be set by the manufacturer, user or through a lookup table.

Figure 16:
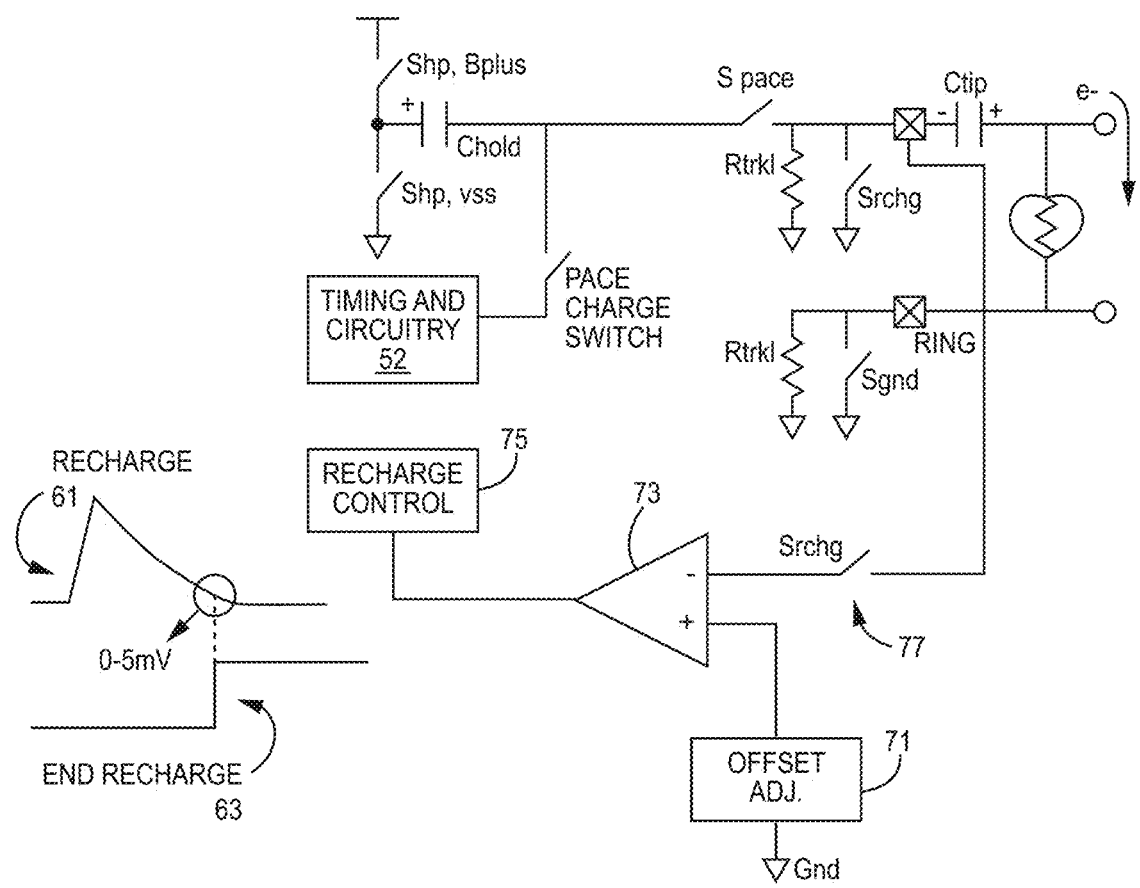
FIG. 16 depicts a simplified view of a portion of the switching matrix from FIGS. 3A-3C in which the recharging time period, associated with a coupling capacitor, is adjustable and dependent upon voltage sensed at a pacing site by a pacing electrode.

An adjustable recharge time can be established by using a lookup table or a separate circuit established that associates the recharge time period with each pacing voltage for the pacing current. The net charge can be determined to be zero or about zero (e.g. 5-10 millivolts) at the coupling capacitor by measuring the voltage at the pacing electrode. Once the net charge can be determined to be zero or about zero (e.g. 5-10 millivolts) at the pacing electrode, the recharge current is automatically terminated using the circuit in FIG. 16. FIG. 16 is the same as FIG. 12A-C. The descriptions of FIGS. 12A-C are incorporated by reference herein except as to electronic components that are added to terminate the recharge pacing pulses once the pacing electrode senses that the voltage at the tissue interface is zero or nearly zero volts (e.g. 5-10 millivolts). The added electronic components include offset adjustment 71, comparator 73, recharge control 75, switch $S_{rchg}$ 77. As shown, the recharge current begins at start time 61 when Srchg closes but the recharge current terminates at end time 63. End time 63 occurs as a result of a control signal generated from recharge control 75. Recharge control 75 could also be configured to be within timing and control module 53. The control signal terminating the recharge signal at end time 63 is generated in response to detection of zero or about zero (e.g. 5-10 millivolts) by the pacing electrode that delivered the pacing pulses to the pacing site. Detection of the lower voltage value by the pacing electrode is determined via comparator 73. Once the control signal is generated, the Srchg opens, which creates an open circuit thereby stopping the recharge process.

The recharge time period for each coupling capacitor can depend upon the characteristics of the pace current (e.g. pacing pulsing width, pacing amplitude, and pacing impedance). The recharge lookup table can use estimated times to ensure the net charge is zero or about zero for each coupling capacitor. An exemplary recharge lookup table can comprise recharge time periods established for each tip capacitor. Each recharge time period is associated with pacing pulse width, pacing amplitude, and pacing impedance. By acquiring one or all of the characteristics (e.g. pacing pulse width, pacing amplitude, and pacing impedance etc.), the recharge time period can be acquired from the lookup table and automatically implemented. Implementing adjustable time periods can conserve energy of the implantable medical device.

Following the pace and recharge operations, the lead system is held in a trickle charge operation in which trickle resistors Rtrkl 112 drain residual charge or polarization artifacts that may remain on the electrode after delivery of the pacing pulse. During a trickle charge operation, the anode (e.g. ring electrodes, device case (IPG only)) are connected to VSS via high impedance trickle resistors. In addition, all of the tip capacitor cathodes are connected to VSS via high impedance resistors 112 of the same value.

The detailed description of FIGS. 12A-12C relative for the atrial tip to atrial ring electrodes can be applied the same or similarly to the remaining exemplary pacing vectors, formed by a cathode and an anode depicted in FIGS. 3A-3C, relative to its pacing and recharging paths. For example, another exemplary pacing vector may comprise the RV tip electrode 142b (i.e. cathode) and the RV ring electrode 116c (i.e. anode). Timing and control circuitry 52 signals switching matrix 58 to deliver a pacing pulse. The switch $S_{hp,vss}$ 122b, associated with the RV tip electrode 142b channel, closes. Thereafter, the switch $S_{pace}$ 106c and $S_{gnd}$ 118c close. When switch $S_{gnd}$ 118c closes, the RV ring electrode 116c is at the same or about the same voltage as Shp Vss. Output capacitor $C_{hold}$ 130b discharges energy to RV tip electrode 142b that has a return path (not shown) to the RVRING 116c (i.e. anode).

To remove the charge on coupling capacitor $C_{tip}$, a passive recharge signal is generated to balance the total charge to a net zero charge. Timing and control circuitry 52 signals switching matrix 58 to perform passive recharge through a set of switching sequences. For example, the $S_{pace}$ switch 106c is opened which creates an open circuit between output capacitor $C_{hold}$ 130b and the RVTIP and RVRING electrodes 142b, 116c thereby stopping the pacing operation. Thereafter, switches $S_{gnd}$ 118c or $S_{hp}$ 122b are opened. This switching sequence keeps the RV ring electrode 116c connected to a circuit reference (i.e. VSS) until after the output capacitor $C_{hold}$ voltage is disconnected from the RV tip and RV ring electrodes 142b, 116c via the $S_{pace}$ switch 106c being opened.

Switch $S_{rchg}$ 124b closes which causes the tip capacitor $C_{tip}$ 132b used in the prior pacing operation to then be connected to reference voltage VSS. After the tip capacitor $C_{tip}$ 132b is connected to negative supply voltage VSS, the RV ring electrode 116c is reconnected to supply voltage VSS via switch $S_{gnd}$ 118c. Once both switches $S_{rchg}$ 124b $S_{gnd}$ 118c are closed, the recharge current path is completed through the external load. Current flow for the recharge path is the opposite direction of the pace current. The total net charge at the coupling capacitor is now zero charge.

Numerous pacing vectors can be formed using left ventricular electrodes 30, 32, 34, 36. One or more of the left ventricular electrodes 30, 32, 34, 36 can be configured to serve as a cathode or an anode. Typically, the left ventricular electrodes 30, 32, 34, 36 are selected as cathodes to pace the LV while the housing (i.e. referred to as a can or case) or the defibrillation electrode 24 serve as the anode. In one or more embodiments, the remaining LV electrodes are deactivated by keeping the $S_{gnd}$ switch open that is associated with the LV electrode. Keeping the $S_{gnd}$ switch, associated with an electrode, open prevents current passing through the circuit for that electrode. In one or more other embodiments, one or more of the remaining electrodes can serve as anode. Additionally, or alternatively, any electrode path can be used for sensing.

Preferably, the electrodes 32 and 34 (FIG. 1) are selected to pace; however, any pair combination of the LV electrodes can be used to pace the left ventricle. In one or more embodiments, electrodes 32 and 34 are spaced 1.5 millimeters (mm) apart while 30 and 36 are 20 to 21 mm spaced apart, as shown in U.S. patent application Ser. No. 13/464,181 filed on May 4, 2012 by Ghosh et al., commonly assigned by the assignee of the present disclosure, the disclosure of which is incorporated by reference in its entirety herein.

Generally, an electrode is selected to serve as a cathode to pace tissue by employing the switching sequence described relative to FIG. 12A-12B to close switches $S_{hp}$ $V_{ss}$ 122, $S_{pace}$ 106, $S_{gnd}$ 118. For an electrode to serve as an anode, $S_{gnd}$ must be closed and $S_{pace}$ is opened. To balance the charge at $C_{tip}$ after pacing the tissue, a recharging current is delivered by opening $S_{pace}$ switch and closing switches $S_{hp}$, $S_{BPLUS}$ 120, $S_{Rrchg}$ 124 $S_{gnd}$, 118 using the switching sequence described relative to FIG. 12C for that particular electrode.

Exemplary paths for a LV electrode to function as a cathode or an anode is now described. Referring to FIG. 3A, LVTIP 116d can be configured to serve as a cathode by closing switch $S_{hp}$ $V_{ss}$ 122c, which is associated with the LV tip electrode channel. Thereafter, the switch $S_{pace}$ 106e to LVHM 104c and $S_{gnd}$ 118f close channel(s) associated to one or more of LVRING 116e/case/RV coil 116a. Switch $S_{gnd}$ 118f and $S_{gnd}$ 118 associated with the channel for the selected anode (e.g. one or more of LVRING/case/RV coil), closes. Switch $S_{gnd}$ 118f and $S_{gnd}$ 118 close at the same or about the same voltage potential as Shp Vss. $C_{hold}$ 130c discharges energy to LVTCAP 110c, $C_{tip}$ 132c, LVTIP 116d that has a return path (not shown) to the LVRING (i.e. LVRING1-3 116e-g as an anode), case or RV coil (i.e. anode).

To remove the charge on coupling capacitor $C_{tip}$, a passive recharge signal is generated to balance the total charge to a net zero charge. Timing and control circuitry 52 signals switching matrix 58 to perform passive recharge. The $S_{pace}$ switch 106e is opened which creates an open circuit between Chad 130c and the electrodes thereby stopping the pacing operation. Thereafter, switches $S_{gnd}$ 118f or $S_{hp}$ 122c are opened. This switching sequence keeps the selected anode (e.g. one or more of LVRING/case/RV coil) connected to a circuit reference (i.e. VSS) until after the output capacitor $C_{hold}$ 130c voltage is disconnected from the LVTIP 116d and one or more electrodes serving as anodes via the $S_{pace}$ switch 106e being open. The one or more anodes may be the case, defibrillation coil, or one of the LV electrodes. The one or more electrodes are selected to serve as an anode by ensuring that the $S_{hp,\ vas}$ and $S_{gnd}$ 118 associated with that electrode is closed during a pacing operation.

After the pacing operation is terminated (i.e. $S_{pace}$ switch is opened), switch $S_{rchg}$ 124c closes which causes the tip capacitor $C_{tip}$ 132c used in the prior pacing operation to then be connected to reference voltage VSS. After the tip capacitor $C_{tip}$ 132c is connected to negative supply voltage VSS, the desired electrode, serving as the anode, is reconnected to supply voltage VSS via switch $S_{gnd}$ 118 that is associated with the channel directly aligned with that particular electrode. For example, if LVRING1 116e is to serve as the anode, $S_{gnd}$ 118g is closed. LVRING electrodes not serving as anode have an open $S_{gnd}$ switch. Alternatively, if LVRING2 116f is to serve as the anode, $S_{gnd}$ 118h is closed. Alternatively, if LVRING3 116g is to serve as the anode, $S_{gnd}$ 118i is closed.

Once switches $S_{rchg}$ 124c and $S_{gnd}$ are closed, the recharge current path is completed through the external load. Current flow for the recharge path is the opposite direction of the pace current. The total net charge at the coupling capacitor is now zero charge.

For LVRING1 to serve as a cathode, switch Shp Vss 122c, associated with the LV ring1 electrode channel, closes. Thereafter, the switch $S_{pace}$ 106g and $S_{gnd}$ 118a close to the case/RV coil. When switch $S_{gnd}$ 118g closes, the case or RV coil or another LV electrode, serves as the anode, which is at the same or about the same voltage potential as $S_{hp}\ V_{ss}$. Chou 130c discharges energy to LVR1TCAP 110d and $C_{tip}$ that has a return path (not shown) to the anode (e.g. case, RV coil etc.)

For LVRING2 to serve as a cathode, switch Shp Vss 122c, associated with the LVRING2 electrode channel, closes. Thereafter, the switch $S_{pace}$ 106i and $S_{gnd}$ 118a close to the case/RV coil. Chou 130c discharges energy to LVR2TCAP 110e (i.e. cathode) that has a return path (not shown) to the case or RV coil (i.e. anode).

For LVRING3 to serve as a cathode, switch Shp Vss 122c, associated with the LVRING3 electrode channel, closes. Thereafter, the switch $S_{pace}$ 106k 104c and $S_{gnd}$ 118a close to the case/RV coil. When switch $S_{gnd}$ 118a closes, the case or RV coil, serves as the anode, which is at the same or about the same voltage potential as Shp Vss. $C_{hold}$ 130c discharges energy to LVR3TCAP 110f (i.e. cathode) that has a return path (not shown) to the case or RV coil (i.e. anode).

Figure 4:
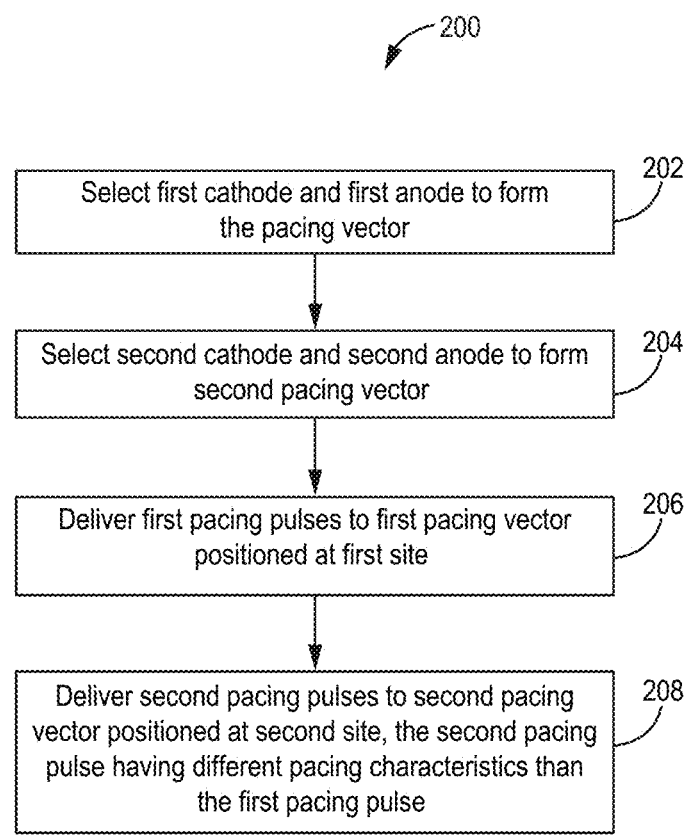
FIG. 4 is a flow chart of a method for selecting electrodes to deliver multi-site pacing therapy.

While switching matrix 58 has been described for a bipolar pace configuration, a unipolar pace can also be used such as a tip (i.e. cathode) to case (i.e. anode). Exemplary values for each electronic component in switching circuit 58 includes $C_{hold}$ at 10 microFarads while $C_{tip}$ is nominally 6.8 microFarads. Trickle resistor 112 values are register-selectable between 5 megaohm (MO) and 500 kiloohm (kΩ) values. FET switches are employed with on resistance to switch (RON) at about 20 ohms. FIG. 4 is a flow diagram depicting a method 200 for controlling a multi-site pacing therapy being delivered from a multi-polar electrode such as an implantable LV lead extending from an implantable medical device. At block 202, a first cathode and a first anode are selected to form a first pacing vector. The first pacing vector is located at a selected first pacing site within a given heart chamber, which may be an LV pacing site. For the sake of illustration, the methods for selecting multiple pacing sites are presented in the context of selecting multiple pacing sites along the LV for CRT therapy. However, the methods described may be altered or adapted as appropriate for selecting pacing sites in or on a different cardiac tissue, heart chamber or tissue and/or for use in a different pacing therapy.

The selection of the first pacing site at block 202 may be based on a variety of measurements or be a nominal pacing site. For example, the first pacing site may be selected as the electrode site corresponding to a late activation time of the LV without LV pacing. A LV activation time is the time interval measured from a reference time point to a sensed R-wave at the pace/sense electrode site. The reference time point may be an atrial sensed or paced event, an R-wave sensed in the RV or a fiducial point. The fiducial may be the onset of QRS (e.g. a QRS complex sensed in the RV) the peak of QRS (e.g. minimum values, minimum slopes, maximum slopes), zero crossings, threshold crossings, etc. of a near or far-field EGM), onset of application of a pacing electrical stimulus, or the like.

A late activation is an activation that occurs relatively later than activation (myocardial depolarization) at other possible LV pace/sense electrode locations. A late activation is not necessarily the latest LV activation that can be measured in the LV since prolonged activation may be associated with pathological or diseased tissue such as myocardial scar tissue, which would be undesirable as a pacing site. With respect to CRT, the greatest therapeutic benefit may be achieved when the LV is paced at or near a location associated with late intrinsic activation time of the ventricle. To determine an electrode site corresponding to late activation, LV activation times are measured at each of the available LV electrodes relative to a reference time point, such as a sensed R-wave in the RV when no ventricular pacing is delivered. In one embodiment, the LV activation times are measured by sensing for an LV depolarization wavefront (R-wave) at each of the LV electrodes 30, 32, 34 and 36 used as sensing electrodes. LV activation times may be measured during an intrinsic rhythm or during atrial pacing. Typically pacing in the RV will be withheld to obtain the LV activation time measurements during intrinsic ventricular conduction.

The first pacing site may be selected using other measurements or techniques, which may or may not be combined with measuring LV activation times. For example, hemodynamic measurements may be performed to determine which pacing site results in the greatest hemodynamic benefit. Hemodynamic measurements may be obtained from other physiological sensors 70 coupled to IMD 10 or using clinical techniques such as Doppler echocardiography, fluoroscopy, or LV catheterization. Exemplary methods to select the most optimal electrodes from which to pace can be determined from, for example, U.S. patent application Ser. No. 13/301,084 filed on Nov. 21, 2011 by Demmer et al., and U.S. patent application Ser. No. 13/464,181 filed on May 4, 2012 by Ghosh et al., commonly assigned by the assignee of the present disclosure, the disclosure of which is incorporated by reference in their entirety herein.

At block 204, a second cathode and a second anode are selected to form a second pacing vector. Selection of the second cathode and the second anode to serve as the second pacing vector uses one or more of the methods presented in block 202. At block 206, first pacing pulses are delivered to the first pacing vector positioned at a first pacing site along a heart chamber. At block 208, second pacing pulses are delivered to the second pacing vector positioned at a second pacing site along a heart chamber. The second pacing pulse is different than the first pacing pulse. For example, the first and second pacing pulse can have different energy characteristics (e.g. voltage, amplitudes, etc.)

The first and second pacing pulses are delivered during the same cardiac cycle. Specifically, first and second pacing pulses are delivered at the same or substantially same time through two or more different electrodes located at different tissue sites. For example, a first pacing pulse having a pre-specified voltage (also referred to as a first voltage) is delivered to a first tissue site followed by a very small or staggered period of time (i.e. 2.5 ms etc.) that starts immediately after generating the first pacing pulse. After the staggered time period ends or expires (e.g. 2.5 ms measured from the generation of the first pacing pulse), a second pacing pulse is generated at a pre-specified voltage (also referred to as a second voltage) and delivered to another tissue site. The staggered time period between the generation of the first and second pacing pulses allows polarization artifacts to be removed from the sensing electrode. Polarization artifacts, generated from the delivery of the pacing pulse, must be cleared or substantially cleared from the electrode before delivery of another pacing pulse; otherwise, the evoked response can be difficult to detect. The staggered time period placed between the pacing pulses emanating from the first and second electrodes ensures that there is a single output associated with each pacing pulse thereby preventing one pacing pulse (e.g. 3 volts) from overlapping with another pacing pulse (e.g. 5 volts). The first and second pacing pulses possess different energy characteristics which allows the pacing to be customized to each patient's needs while seeking to reduce power consumption by using, for example, 3 volts instead of 5 volts.

One or more embodiments relate to recharging the coupling capacitor associated with the switching matrix 58. The timing and control circuitry 52 signals the switching matrix 58 to generate a pacing pulse via an output capacitor, as described relative to FIGS. 12A-12B. The signal causes a set of switches to discharge the output capacitor, which transmits the energy (e.g. pacing pulse) to the electrode. After the pacing pulse terminates, a recharging current is generated to obtain zero or about zero net charge at the coupling capacitor, as previously described relative to FIG. 12C, and incorporated herein.

Programmable pacing parameters, shown in a graphical user interface (GUI) 300 of FIG. 5, can affect recharging times of coupling capacitors. Programmable pacing parameters control device function and/or data collection. Programmable pacing options used by IMD 10 to deliver therapy include, for example, ventricular pacing, interventricular (V-V) pace delay, or multiple point LV delay. The left-hand column of the programmable pacing options of GUI 300, designated as "initial value," are typically pre-set at a desirable goal while the right hand side column, designated as "optimized permanent," is set by the user to reflect actual information related to the patient.

Ventricular pacing parameter determines whether a ventricle(s) is paced and in which order each ventricle is paced. The ventricular pacing parameter allows for selection of pacing of the RV followed by pacing the LV (i.e. RV→LV), pacing of the LV followed by pacing of the RV (i.e. LV→RV), LV only pacing, or RV only pacing. The ventricular pacing parameter is selected based upon the cardiac condition of the patient to achieve maximum cardiac output.

The V-V pace delay controls the timing interval between the RV and LV1 paces when RV+LV order is selected and between LV1 and RV paces when LV+RV order is selected. V-V pace delay parameter can be set at any time such as up to 100 ms after the first pacing pulse (e.g. 1: 0 (=2.5), 0 ms, 10 ms, . . . 80 ms etc.). Multiple point LV delay is defined as the delay that exists between the first and second LV pacing pulses that are delivered to the first and second LV pacing sites, respectively.

Ventricular pacing can be implemented, for example, by pacing of the RV followed by pacing the LV (i.e. RV→LV). Once the ventricular pacing parameter has been selected, the V-V pace delay is pre-specified to a certain value (e.g. greater than or equal to 10 ms etc.). Multiple point LV delay, linked to V-V pace delay through a lookup table, using the values set forth in Table 1, requires the multiple point LV delay to be greater than or equal to 10 ms. After ventricular pacing and the V-V delay are designated, the sequence of recharging coupling capacitors, exemplarily shown in FIGS. 3A-3C, is automatically set in a specified order, as summarized in Table 1. For example, assume that ventricular pacing is set to pacing the RV followed by pacing the LV (i.e. RV→LV), and V-V pace delay is set at 10 ms, the multiple LV delay is set to being greater than or equal to 10 ms, then the first coupling capacitor, associated with delivering the electrical stimuli for the first LV pace, is immediately recharged after the first LV pace. The second coupling capacitor is immediately recharged after delivery of the electrical stimuli for the second LV pace. The capacitor associated with delivering the RV pace is immediately recharged after delivery of the RV pace.

In another embodiment related to ventricular pacing of the RV followed by pacing the LV (i.e. RV→LV), and V-V pace delay is set at about 2.5 ms, the multiple LV delay is set to being greater than or equal to about 20 ms. The first capacitor and the RV capacitor are recharged after delivery of the first LV pace. The second capacitor is recharged after delivery of the second LV pace.

In yet another embodiment related to ventricular pacing of the LV followed by pacing the RV (i.e. LV→RV), the V-V pace delay is set at greater than or equal to about 20 ms, the multiple LV delay is set to being greater than or equal to about 10 ms. The first capacitor is recharged after delivery of the first LV pace. The second capacitor is recharged after delivery of the second LV pace. The RV capacitor is recharged after delivery of the RV pace.

In still yet another embodiment related to ventricular pacing of the LV followed by pacing the RV (i.e. LV→RV), and V-V pace delay is set at about 20 ms, the multiple LV delay is set to about 2.5 ms. The first capacitor is recharged after delivery of the second LV pace. The second capacitor is recharged after delivery of the second LV pace. The RV capacitor is recharged after delivery of the RV pace.

In yet another embodiment related to ventricular pacing of the LV followed by pacing the RV (i.e. LV→RV), and V-V pace delay is set at 2.5 ms, the multiple LV delay is set to 2.5 ms. The first capacitor is recharged after delivery of the second RV pace. The second capacitor is recharged after delivery of the first LV pace. The RV capacitor is recharged after delivery of the RV pace.

First LV pace recharge refers to the capacitor, associated with the first LV electrode, recharging after a first pace or first pacing pulse (i.e. energy discharge) is delivered to cardiac tissue (e.g. ventricle) which typically takes about 20 milliseconds (ms). Second LV pace recharge refers to the capacitor recharging after a second pace or second pacing pulse. RV pace recharge refers to the capacitor recharging after a pacing pulse to the RV.

Optionally, restrictions can be applied during CRT therapy to one or more embodiments. Multisite LV pace polarity and LV first pace polarity cannot both use the RV coil unless recharge is completed because the potential for additional polarization is eliminated on the possible sensing path. If LV→RV is selected with V-V delay set to 0 (i.e. a staggered time period of about 2.5 ms) and multiple point LV pacing is switched ON, multiple point LV delay is not selectable, which will result in LV-2.5 ms-LV-2.5 ms-RV.

In one or more other embodiments, if LV→RV is selected, the V-V delay of 10 ms is not allowed. In one or more other embodiments, if RV→LV is selected, multisite LV delay of 0 or 10 ms is also not allowed. In contrast, if LV→RV is selected and multisite LV pacing is ON, multiple point LV delay is required to be less than V-V delay. In one or more embodiments, if CRT is adaptive, ventricular pacing and V-V pace delay cannot be selected or programmed.

Table 1, presented below, summarizes the programmable options that may be used by IMD 10.
Table 1 presents device CRT parameters along with exemplary values that can be programmed into implantable medical device.

| | | | IMD Parameter | | |
|---|---|---|---|---|---|
| Ventricular pacing Mode | V-V pace delay | Multiple point LV delay | First LV pace recharge | Second LV pace recharge | RV pace recharge |
| RV→LV | ≥10 ms | ≥10 ms | After first LV pace | After second LV pace | After RV pace |
| | 2.5 ms | ≥20 ms | After first LV pace | After second LV pace | After first LV pace recharge |
| LV→RV | ≥20 ms | ≥10 ms | After first LV pace | After second LV pace | After RV pace |
| | ≥20 ms | 2.5 ms | After second LV pace recharge | After second LV pace | After RV pace |
| | 2.5 ms | 2.5 ms | After RV pace recharge | After first LV pace recharge | After RV pace |

In addition to Table 1, timing diagrams, presented in FIGS. 6-11, provide useful examples as to varied recharging times of coupling capacitors after delivery of pacing pulses to cardiac tissue. Each timing diagram such as timing diagram 400 shown in FIG. 6 includes six horizontal lines 402-412. The top three horizontal lines 402, 404, 406 show timing of different pacing pulses while the bottom three horizontal lines 408, 410, 412 show the recharging times for each coupling capacitor associated with a channel to a particular electrode (e.g. RV electrode, LV1 electrode, LV2 electrode etc.). Recharging time for each coupling capacitor is affected by one or more pacing pulses. Vertical lines 414, 416 intersecting a pacing pulse horizontal line indicates either the start time 414 or ending time 416 of the pacing pulse. The time between the start and end of the pacing pulse is the duration of the pacing pulse. Similarly, the vertical lines 418, 420, along one of the bottom recharging horizontal lines indicates either the start time 418 or ending time 420 of the recharging operation. The duration of the recharging operation occurs between the start and end times for recharging. The timing diagram is interpreted by reviewing the pacing pulse line and then the related recharging line. Any pacing pulse that interrupts a recharging time is then examined.

Generally, recharging of the coupling capacitor follows a set of recharging requirements. For example, after a pacing pulse is delivered, the recharging operation continues unless the recharging operation gets interrupted by another pacing pulse. The last pace gets top priority for completing its associated recharging operation unless that particular recharging operation is interrupted by another pace. Additionally, the last pace is the first to finish its recharging operation because no other pacing pulse will interrupt the recharging operation associated with the last pace during the pacing interval.

The set of recharging requirements applies to a group of paces such as the RV pace, the first LV pace, and the second LV pace shown in FIGS. 6-11. The corresponding time between groups is considered to be the overall pacing interval. For example, if the pacing interval is 1000 msec (60 beats/minute), the time between one RV pace and the next RV pace (not shown) is 1000 msec, while the time between the RV pace and the first and second LV paces involves shorter time intervals. Exemplary shorter time intervals between first and second LV paces are shown in the timing diagrams.

Figure 6:
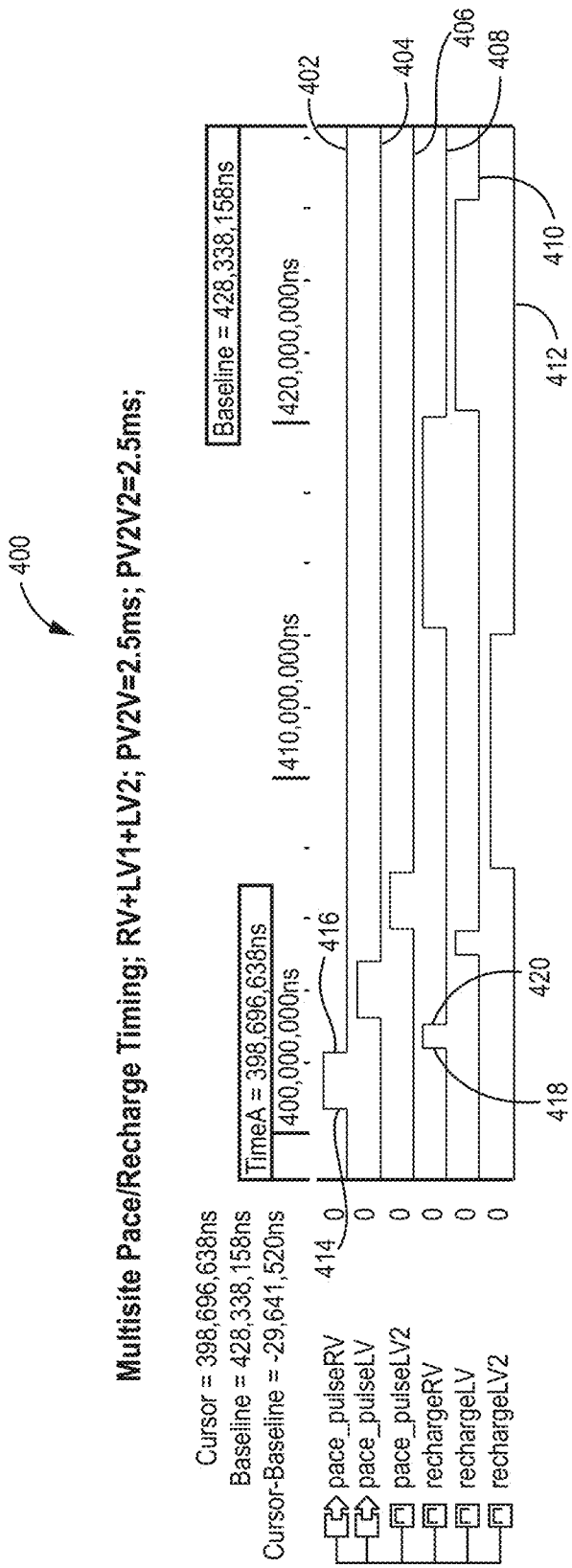
FIG. 6 is a timing diagram that depicts a pacing pulse delivered to a right ventricle, first and second pacing pulses delivered to the left ventricle along with respective coupling capacitor recharge times.

FIG. 6 depicts a timing diagram 400 that begins with a RV pacing pulse being sent to the RV electrode. The RV pace begins at the first vertical line extending from the horizontal line and terminates at the next vertical line from the same horizontal line. The delay between the first and second pace (PV2V) and the delay between the second and third pace (PV2V2) are also shown in FIG. 6. In particular, PV2V is the time between the start of the first pace and the start of the second pace while PV2V2 is the time between the start of the second pace and the start of the third pace. The coupling capacitor, associated with the same channel as the RV electrode, undergoes a set of recharging operations. For example, the coupling capacitor immediately recharges after the RV pacing pulse terminates. The RV coupling capacitor recharging operation is interrupted by a pacing pulse at the LV1 electrode. The coupling capacitor, associated with the same channel as the LV1 electrode, undergoes a recharging operation immediately after the LV1 pacing pulse is completed and continues until the recharging operation is interrupted by the LV2 pacing pulse. The coupling capacitor, associated with the same channel as the LV2 electrode, undergoes a recharging process immediately after the LV2 pacing pulse is completed and continues until completion of the recharging operation. The coupling capacitor associated with the RV1 electrode then completes its recharging operation through a second recharge operation. Thereafter, the coupling capacitor associated with the LV1 completes its recharging operation.

Figure 7:
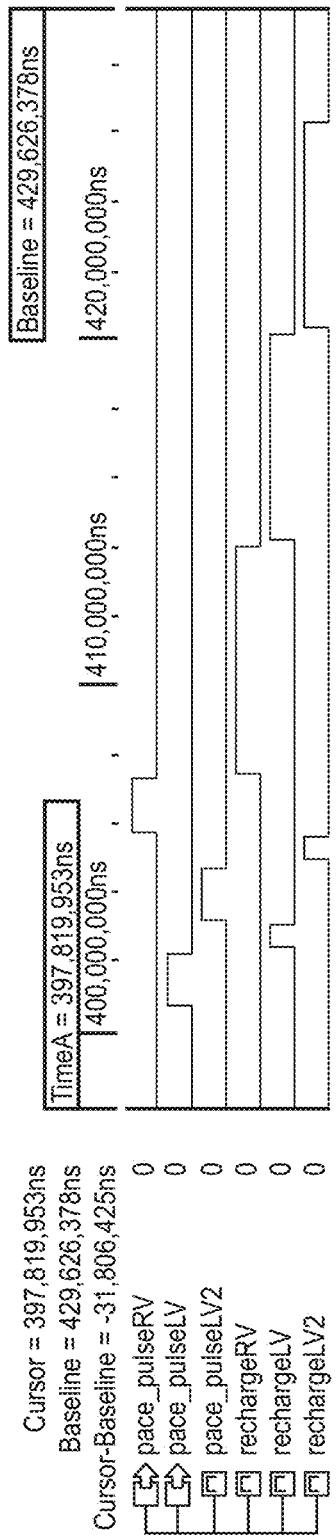
FIG. 7 is a timing diagram that shows a first and second pacing pulse delivered to a left ventricle, a third pacing pulse delivered to the right ventricle along with respective coupling capacitor recharge times.

FIG. 7 depicts yet another timing diagram that begins with a LV1 pacing pulse being delivered to the LV1 electrode. The coupling capacitor associated with the LV1 electrode undergoes a recharge operation immediately after the LV1 pacing pulse terminates. The LV1 recharging operation continues but is interrupted by the LV2 pacing pulse. The coupling capacitor, associated with LV2, begins the recharging operation and continues until the RV pacing pulse interrupts the recharging operation. The coupling capacitor, associated with the RV electrode, begins the recharging operation immediately after the RV pacing pulse is completed. The coupling capacitor associated with the RV electrode completes its recharging operation followed by the coupling capacitor associated with the LV1 electrode completing its recharging operation. After the LV1 recharging operation is completed, the LV2 recharging operation is completed.

Figure 8:
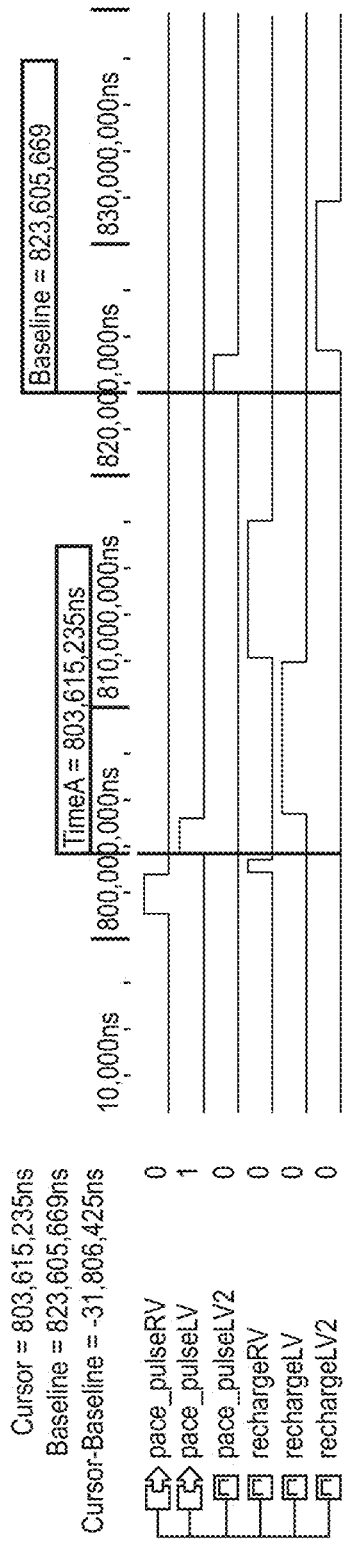
FIG. 8 is a timing diagram that shows a pacing pulse delivered to a right ventricle, first and second pacing pulses delivered to the left ventricle along with respective coupling capacitor recharge times.

FIG. 8 depicts yet another timing diagram that begins with a RV pacing pulse being delivered to the RV electrode. The coupling capacitor, associated with the RV electrode, begins its recharge operation immediately after the RV pacing pulse terminates. The recharging operation continues but is interrupted by the LV1 pacing pulse. The coupling capacitor associated with the LV1 starts its recharge operation after the pacing pulse terminates and continues to completion. The pacing pulse for LV2 is then delivered. The coupling capacitor, associated with the LV2 pace, begins and completes its recharging operation uninterrupted.

Figure 9:
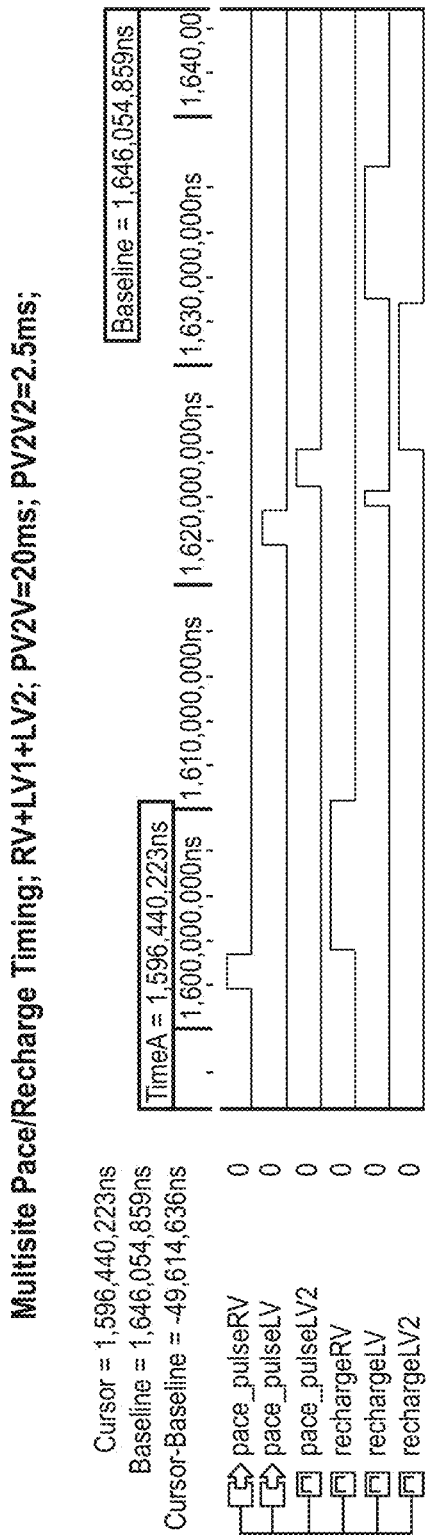
FIG. 9 is a timing diagram that shows a pacing pulse delivered to a right ventricle, first and second pacing pulses delivered to the left ventricle along with respective coupling capacitor recharge times.

FIG. 9 depicts a timing diagram that begins with a RV pacing pulse being delivered to the RV electrode. The coupling capacitor associated with the RV electrode undergoes a recharge operation immediately after the RV pacing pulse terminates. The RV recharging operation is completed uninterrupted. The LV1 pacing pulse is delivered. The coupling capacitor, associated with the LV1 electrode, begins its recharging operation immediately after the LV1 pacing pulse is completed. The recharging operation for the coupling capacitor associated with LV1 continues until the recharging operation is interrupted by the LV2 pacing pulse. The recharging operation of the coupling capacitor associated with the LV2 pacing pulse begins immediately after the LV2 pacing pulse is completed. The LV2 coupling capacitor recharging operation is then completed. Thereafter, the LV1 recharging operation is completed.

Figure 10:
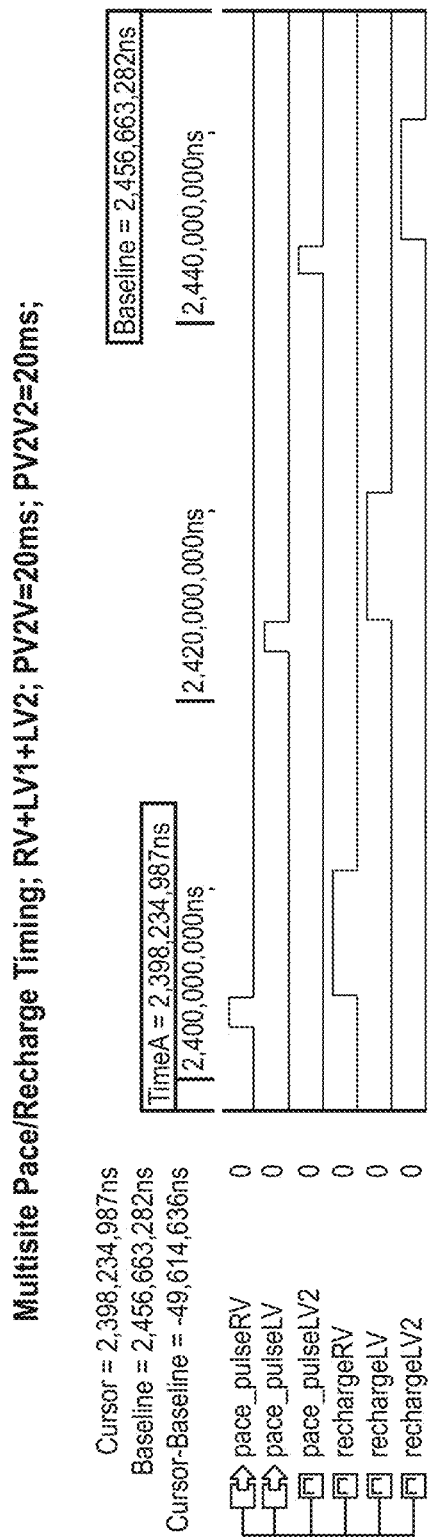
FIG. 10 is a timing diagram that shows a pacing pulse delivered to a right ventricle, first and second pacing pulses delivered to the left ventricle along with respective coupling capacitor recharge times.

FIG. 10 depicts a timing diagram in which the recharging operations continue without interruption by another pacing pulse. The RV pacing pulse is delivered to the RV electrode. The coupling capacitor, associated with the RV electrode, undergoes a recharge operation immediately after the RV pacing pulse terminates. The RV recharging operation continues until completion. The LV pace is then delivered followed by the recharging operation of the coupling capacitor associated with the LV. The recharging operation is completed before the LV2 pace is delivered to the LV2 electrode. After the LV2 pace is delivered, the LV2 recharging operation is begun and eventually is completed without interruption.

Figure 11:
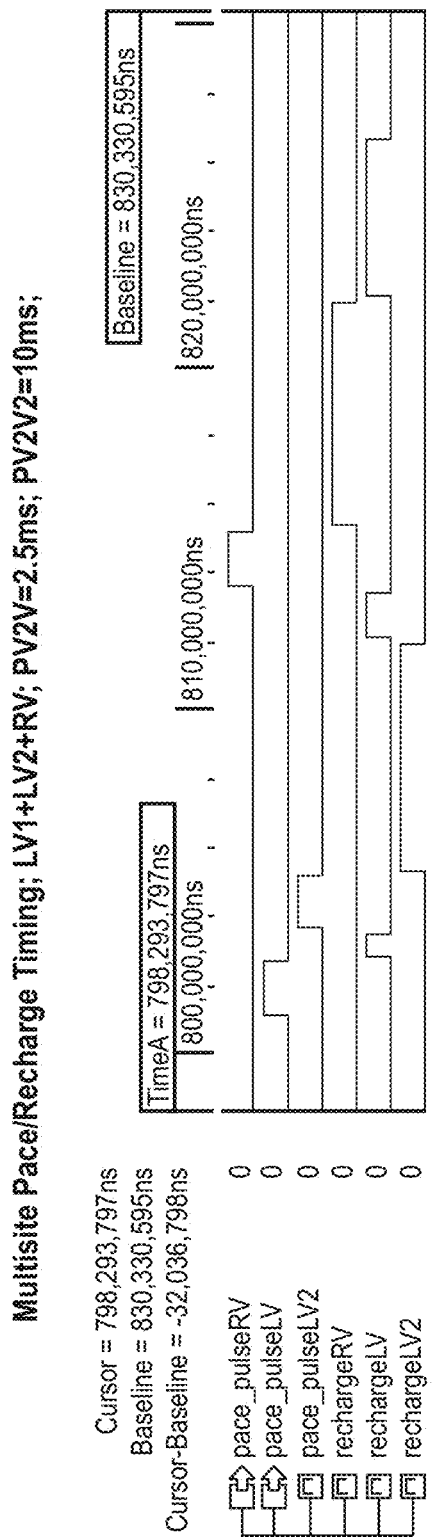
FIG. 11 is a timing diagram that shows first and second pacing pulses delivered to the left ventricle, a pacing pulse delivered to a right ventricle along with respective coupling capacitor recharge times.

FIG. 11 is yet another exemplary timing diagram. A pacing pulse is first delivered to the LV1 electrode. The coupling capacitor associated with the LV1 electrode immediately begins recharging until the recharge operation is interrupted by a pacing pulse associated with the LV2 electrode. The coupling capacitor associated with the LV2 electrode immediately begins recharging after termination of the pacing pulse. The recharge operation for the LV2 coupling capacitor continues unimpeded. The coupling capacitor, associated with the LV1 electrode, again attempts to recharge but is interrupted by the pacing pulse delivered to the RV electrode. The coupling capacitor associated with the RV electrode completes its recharge operation. Thereafter, the coupling capacitor associated with the LV1 electrode finishes its recharge operation.

Method 500, depicted in FIG. 13, verifies effective capture of individual electrodes (e.g. cathodes) during multi-site pacing therapy. As previously explained, multisite pacing involves pacing therapy delivered by stimulation of cardiac tissue from more than one electrode located in the same chamber (e.g. left ventricle) of the heart within the same cardiac cycle, often in close spatial proximity e.g. two electrodes of the multi (quadri)-polar lead within a tributary of the coronary sinus in the left ventricle. Multi-site or multipoint pacing may be delivered by simultaneous or sequential stimulation of two or more electrodes located in the same chamber (e.g. LV). Simultaneous pacing is defined as pacing from two or more electrodes where the timing delay between electrodes is less than 5 ms. Since the electrodes in multi-site or multi-point stimulation are in close proximity to each other, it is important to detect and verify effective capture of individual electrodes during delivery of such therapy. While conventional left ventricular capture management routines determine capture thresholds for each electrode individually during stimulation from each LV electrode, conventional capture management can not verify capture during multi-site or multipoint pacing therapy from more than one LV electrodes. Detection of capture is especially important during sequential multipoint stimulation since too long of inter-electrode timing delay may cause a refractory condition (e.g. cardiac tissue will not respond to electrical excitation) near the second electrode that receives the second pacing pulse. For purposes of clarity, similar reference numbers (e.g. 504*a*,*b* 506*a*,*b*) are used in FIG. 13 to identify similar elements.

Method 500 begins at block 502 in which therapy 502 is delivered to the tissue via pacing pulses to the first and second pacing vectors. For example, the first pacing pulse is delivered to a first pacing site at block 504*a*. The second pacing pulse is delivered to the second pacing site at block 504*b*. It should be understood that while block 504*b* refers to a second pace, block 504*b* contemplates that paces can be delivered to Nth pacing electrode, where N can be any number between 2-10, in order to evaluate effective capture individually from differently placed electrodes during multi-electrode pacing. At block 506*a*, an electrical signal (e.g., morphological waveform(s) within electrograms (EGM)) corresponding to the first LV electrode is windowed for evaluation of effective capture from that same electrode. As used herein, a morphological waveform corresponds to the evoked response to a pacing stimulus measured by the time-variation of electrical potential between the stimulating cathode (e.g. LVx where X relates to any one of the LV electrodes 30, 32, 34, 36 FIG. 1) and an second electrode, which may be an indifferent electrode (e.g. RV Coil). Features of the morphological waveform are analyzed within a predetermined, or selected, time period, or timing window, (e.g., 150 ms, 165 ms, 175 ms, 185 ms, 200 ms) after the delivery of pacing stimulus. For example, the LVx-RV coil EGM represents the unipolar electrogram for each LV cathode employed in stimulation. Block 506*b* involves windowing an electrical signal (e.g., morphological waveform(s) within an EGM) for the delivery of the second pace to the second pacing vector near or in the second pacing site.

At block 508, effective capture criteria is applied to each electrode (e.g. cathode) that delivers energy to tissue. For example, effective capture criteria for each electrode (e.g. LVx electrode) is based on gross morphological features of unipolar LVx-RV coil EGM. Exemplary effective capture criteria or effective capture test (ECT), an example of which may be seen with respect to U.S. Pat. No. 8,750,998 issued Jun. 10, 2014, and assigned to the assignee of the present invention, the disclosure of which is incorporated by reference in its entirety herein. Verification of capture is calculated at each LV cathode individually using features of unipolar electrogram vector e.g. LV cathode-RV coil or LV cathode-can. The method to determine effective capture employs gross features of the electrogram such as maximum amplitude (Max), minimum amplitude (Min), timing of the maximum (Tmax) and minimum (Tmin) amplitudes, baseline amplitude (BL) within a time-window of a pre-specified window (e.g. 165 ms) starting from the time of delivery of the first LV pace and uses criteria, presented below, to verify effective tissue capture.

Figure 14:
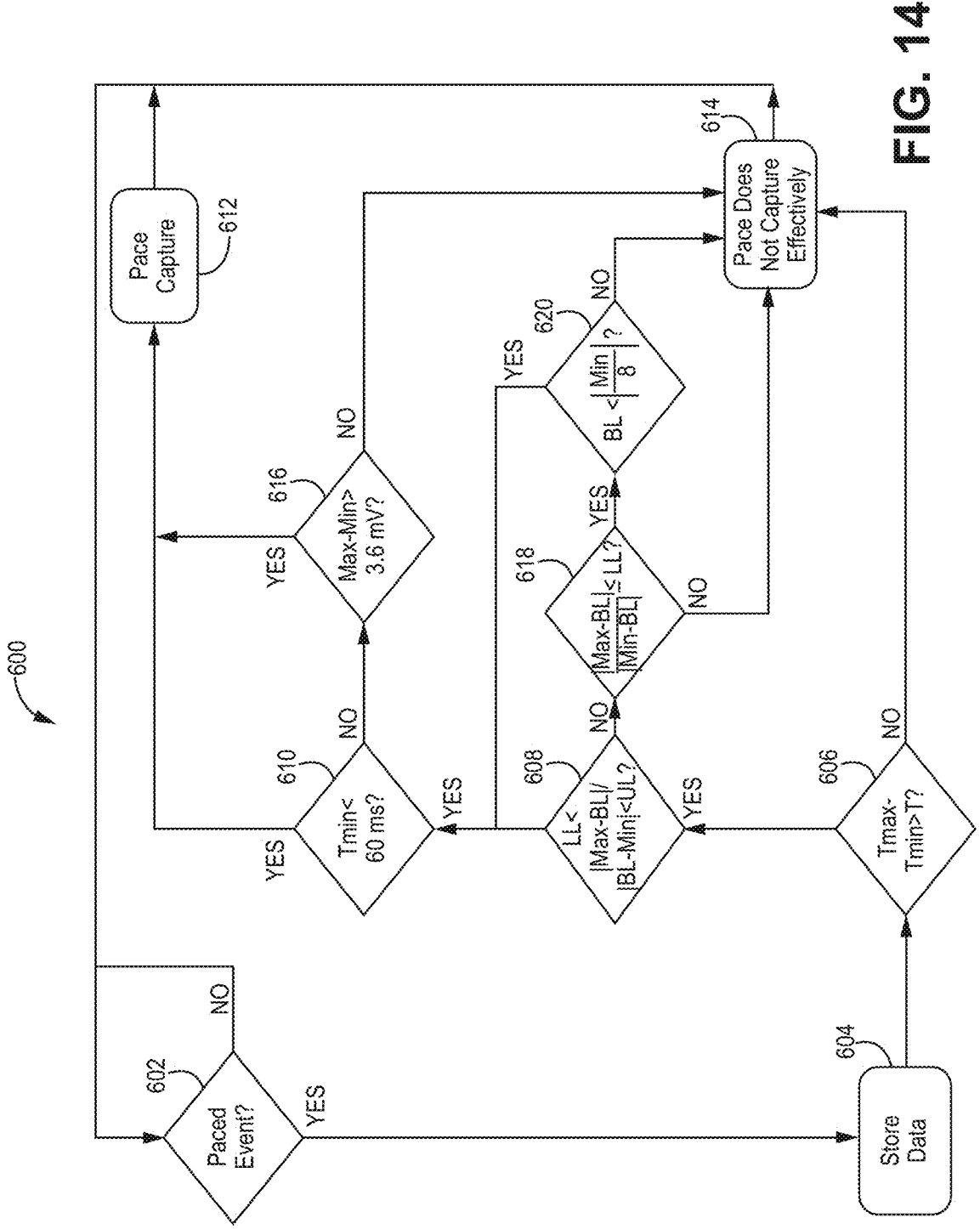
FIG. 14 is a flow diagram depicting in which each electrode is evaluated to determine whether a pace effectively captures cardiac tissue.

FIG. 14 depicts the flow diagram for determining effective capture at a single electrode. Both the first and second electrodes are evaluated using criteria set forth in method 600. To determine whether a pacing stimulus effectively captures a ventricle, sensed data is evaluated according to one or more of the mathematical relationships embodied at blocks 606, 608, 610, 616, 618, and 620. At block 606, a determination is made as to whether a first condition relative to effective capture is met. The first condition, presented below, subtracts Tmin from Tmax and then determines whether the result is greater than a predetermined threshold (T) such as 30 ms. The equation for the first condition is as follows:

$$Tmax-Tmin > \text{Threshold (e.g. 20-35 ms)}$$

If Tmax−Tmin is not greater than 30 ms, then the NO path continues to block 614 in which the pacing stimulus is declared to ineffectively capture a ventricle. In contrast, if Tmax−Tmin>30 ms, the YES path continues to block 608. At block 608, a determination is made as to whether a second condition is met. The equation for the second condition is as follows:

$$LL < |Max-BL|/|BL-Min| < UL.$$

The lower limit (LL) and upper limit (UL) are associated with upper and lower ratio limits, respectively, of a morphological feature. Exemplary LL can be 0.2 with a range of 0.1 to 0.33 and exemplary UL can be 5.0 with a range of 3.0 to 10.0. Preferably, LL is set at 0.125 and the UL is set at 8.0.

The maximum value (Max) and the minimum value (Min) are associated with a particular EGM morphological feature such as amplitude. The ratio, $|Max-BL|/|BL-Min|$, includes the absolute value of Max-BL which is divided by the absolute value of BL-Min. If the second condition at block 608 is not satisfied, then the NO path continues to block 618 in which a determination is made as to whether $(|Max-BL|/|Min-BL|) LL$. If $(|Max-BL|/|Min-BL|) LL$ is not met, then the NO path continues to block 614 and the ventricular pace stimuli is declared not to evoke effective capture of the ventricle. In contrast, the YES path from block 618 continues to block 620 in which a determination is made as to whether $BL<|Min/8|$. If BL is not less than $|Min/8|$, the NO path from block 620 continues to block 614 in which the electrical stimuli is declared to ineffectively capture the ventricle. If BL is less than $|Min/8|$, then the YES path continues to optional block 610.

The YES path from block 608 also continues to block 610 which determines whether Tmin is less than a preselected value such as 60 ms. The preselected value can be any value between 40 ms-80 ms. If Tmin is not less than 60 ms, then the NO path continues to optional block 616 in which another determination is made as to whether Max−Min is greater than a threshold such as any value from 0.5-4.0 mV. If Max−Min is greater than 3.5 mV, effective capture exists and the YES path continues to block 612 in which the ventricular stimulus is declared to capture the ventricle. The NO path from block 616 continues to block 614 in which a determination is made that ventricular stimulus is determined not to effectively capture a ventricle.

Returning to block 610, if Tmin is less than 60 ms, then the YES path continues to block 612 in which effective capture is declared. Every time effective capture is declared at block 612, an effective capture counter is incremented by 1. The effective capture counter is maintained and updated continuously during effective capture monitoring. Effective capture monitoring determines whether pacing stimulus is effective or ineffective. Effective capture monitoring tracks responses from cardiac tissue during pacing therapy.

Effective capture monitoring may be performed continuously or, more preferably, performed periodically (e.g. 100 beats/hour (hr), daily etc.) in order to conserve battery life. Preferably, effective capture monitoring is performed 100 beats per hour and consists of normal pace timings (not the ideal timing conditions of ECT). The effective capture monitoring (i.e. 100 beats per hour) is reported to the user as a % of effective capture beats. The user can apply any choice of threshold for concern (e.g. 90%, etc.). After a period of monitoring, a metric of effective capture can be computed by dividing the effective capture counter by the total number of paced beats. The method then returns to monitoring for the next paced event at block 602.

Figure 13A:
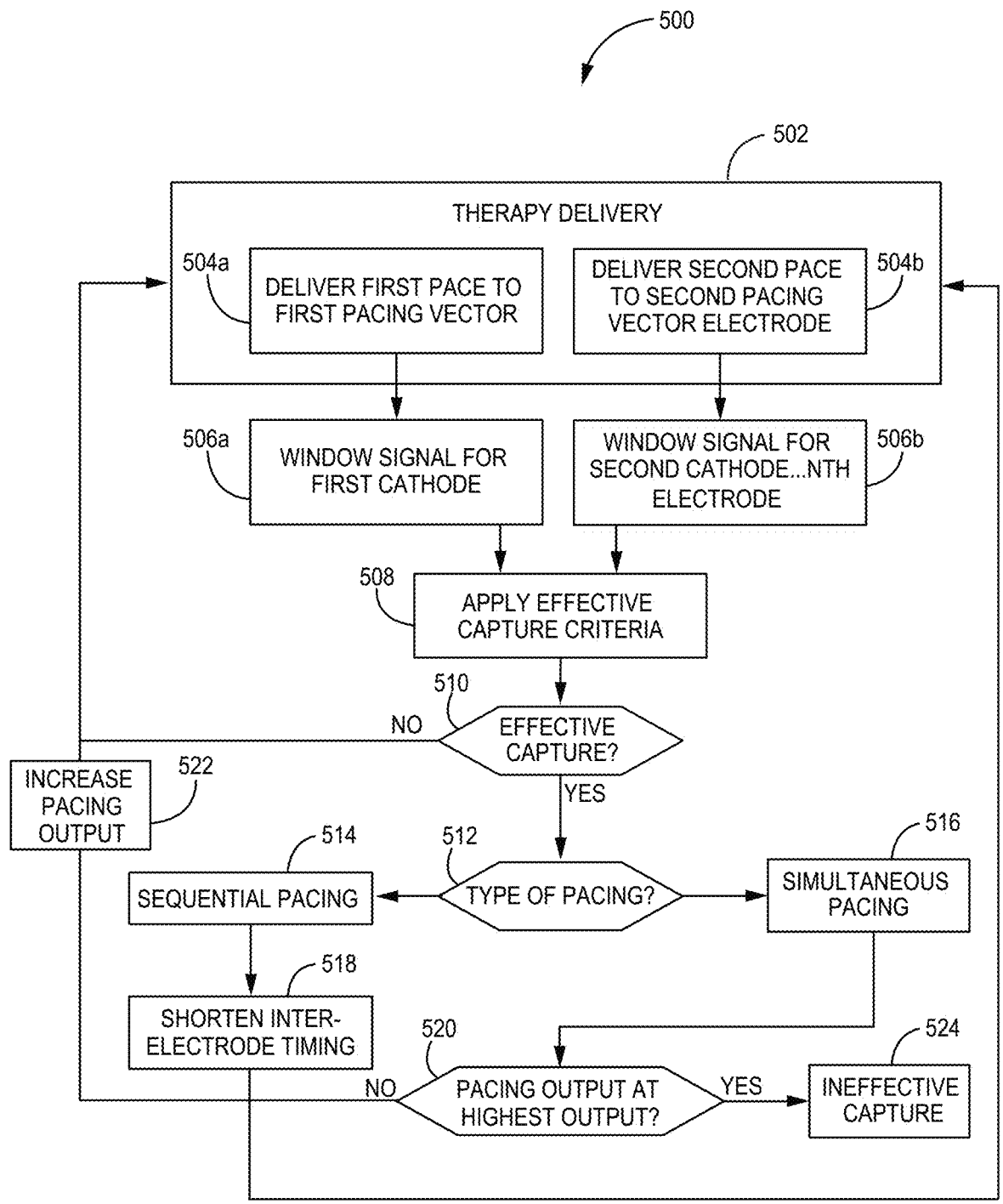
FIG. 13A is a flow diagram depicting a first embodiment related to determining whether multi-point pacing effectively captures cardiac tissue.
Figure 13B:
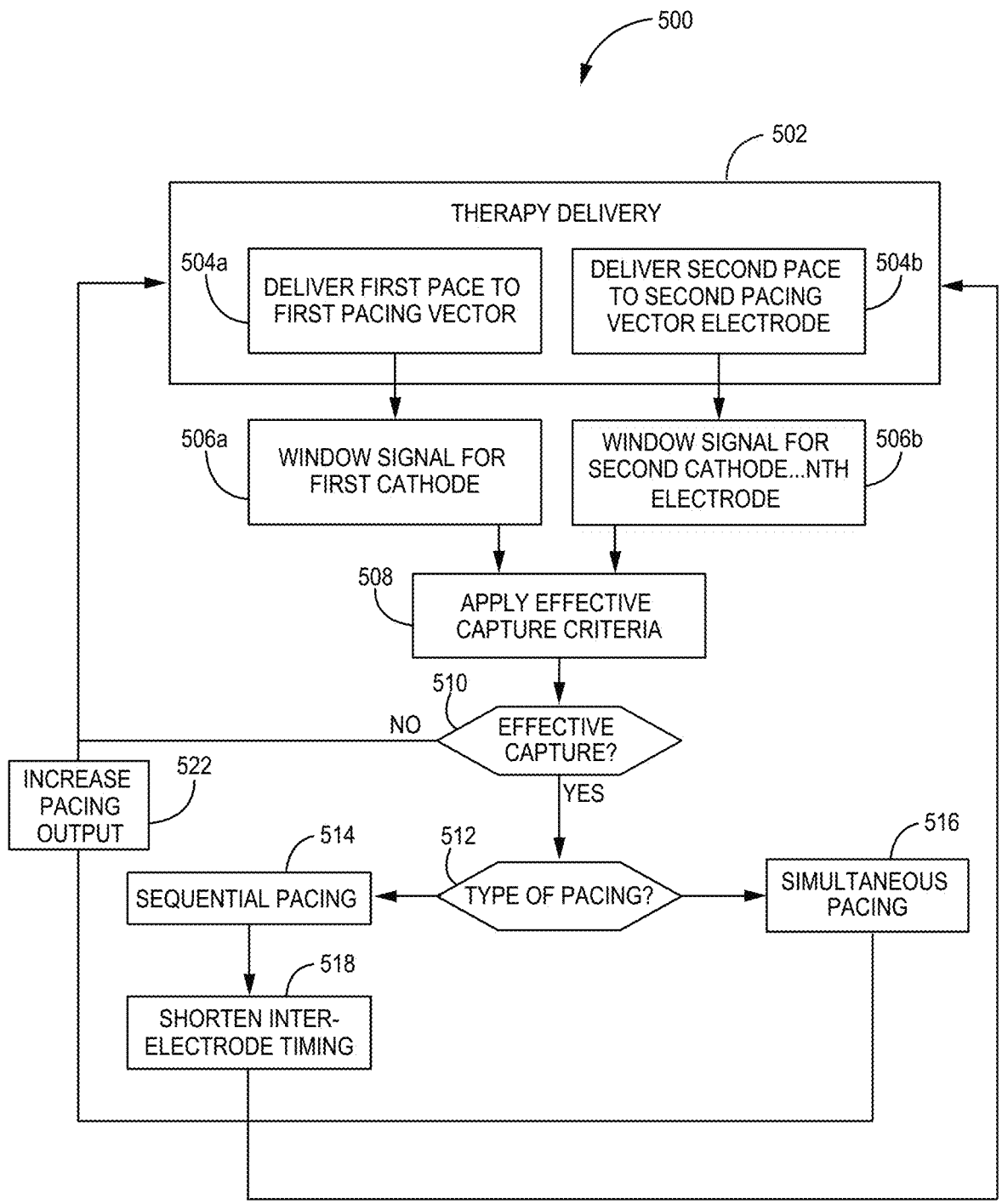
FIG. 13B is a flow diagram depicting a second embodiment related to determining whether multi-point pacing effectively captures cardiac tissue.
Figure 15A:
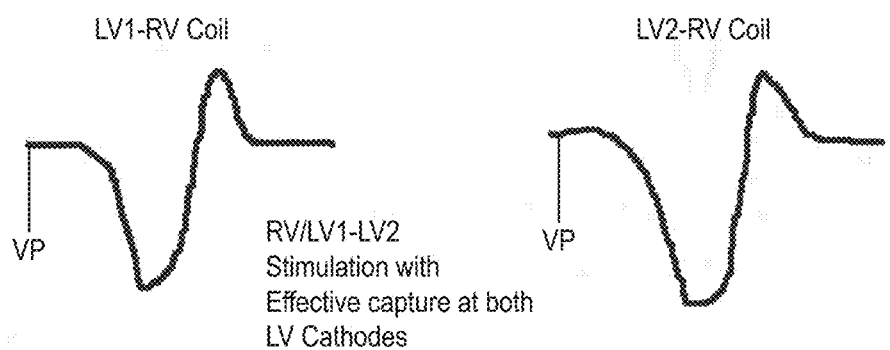
FIG. 15A is a unipolar electrogram measured from a first LV electrode LV1 to an indifferent electrode RV Coil, showing effective capture occurred at a first left ventricular (LV1) electrode.
Figure 15B:
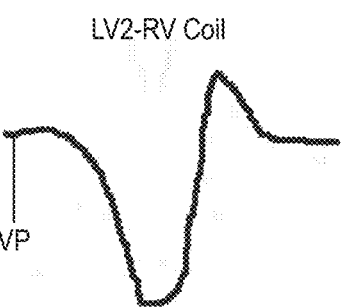
FIG. 15B is a unipolar electrogram measured from a second LV electrode LV2 to an indifferent electrode RV Coil showing effective capture occurred at a second left ventricular (LV2).
Figure 15C:
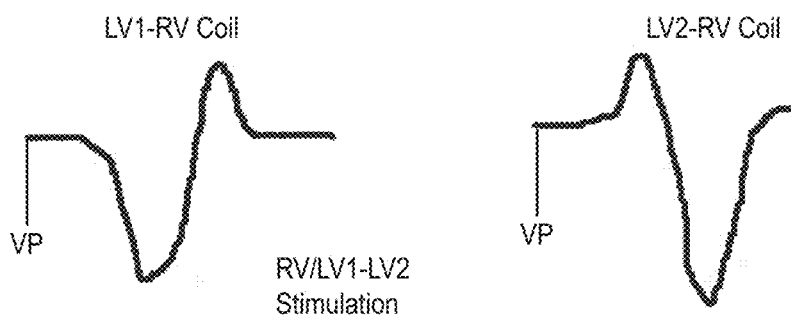
FIG. 15C is a unipolar electrogram measured from the first LV electrode LV1 to an indifferent electrode RV Coil, showing effective capture occurred at a first left ventricular (LV1) electrode.
Figure 15D:
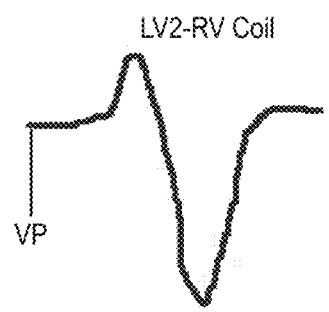
FIG. 15D shows a unipolar electrogram measured from the second LV electrode LV2 to an indifferent electrode RV Coil, showing ineffective capture at the second LV electrode (LV2).

After the first and second electrodes are each evaluated for effective pacing using method 600, a determination is made as to whether effective capture is present at block 510 of FIG. 13A-13B. If neither the first or second paces effectively capture the cardiac tissue, then the NO path returns to block 502 to test one or more other electrodes. If both the first and second paces are effective, at block 510, the paces delivered are declared to be effective and the YES path continues to block 512. FIGS. 15A-15D are unipolar electrogram traces corresponding to LV electrodes (e.g. cathodes) during multisite stimulation. Ventricular pacing starts (VP) at begins at VP in each electrogram. FIG. 15A electrogram shows effective capture occurred at LV1 electrode-RV coil while FIG. 15B shows effective capture occurring at LV2 electrode-RV coil. In contrast, FIGS. 15C-15D depicts effective capture occurring at RV/LV1-LV2 electrodes in FIG. 15C while FIG. 15D shows ineffective capture at LV2-RV-coil. In particular, QS morphology at LV1-RV Coil indicates effective capture at cathode LV1 but r-S morphology at LV2-RV Coil indicates lack of effective capture at cathode LV2.

At block 512 the processor causes the type of multi-site pacing to follow either a sequential pacing 514 path or a simultaneous pacing path set of instructions. For example, if the multi-site pacing is deemed sequential pacing 514, then inter-electrode timing is shortened at block 518 For example, the inter-electrode timing may be altered in decremental steps of 5 ms or 10 ms, i.e. from 40 ms to 35 ms, or from 40 ms to 30 ms. Thereafter, the path continues to block 502 or is stopped for a pre-specified time period.

On the other hand, if the multi-site pacing is deemed simultaneous pacing at block 516, an optional determination block 520 of FIG. 13A is used to determine whether pacing output is at the highest output. The highest output is the maximum amount of energy (e.g. highest amplitude, longest pulse width) delivered by the IMD to the tissue. The YES path from block 520 to block 524 indicates that ineffective capture is occurring which may be due to lead dislodgement or a bad substrate (e.g. scar tissue). Thereafter, another electrode may be evaluated for therapy delivery starting at block 502. Returning to block 520, if pacing output is not at its highest output, then the NO path continues to block 522 and the pacing output is increased.

FIG. 13B is the same as FIG. 13A except that blocks 520 and 524 are removed and simultaneous pacing block connects directly with block 522 in which pacing output is increased. Skilled artisans will appreciate that method 500 detects and confirms effective tissue capture from each individual electrode (e.g. cathode) during multipoint or multisite LV pacing. In particular, method 500 distinguishes steps based on which optimal timing intervals can be set for sequential multi-point pacing compared to simultaneous multi-point pacing.

An implantable medical device, method, or system use a pacing sequence that has total pacing energy less than a conventional single pace (e.g. 5 volts). For example, assume a bipolar medical electrical lead is used to pace one electrode to another electrode. Assume further that 5 volts at 0.5 ms are needed to capture cardiac tissue. One embodiment of the present disclosure contemplates using a precharge and a pace. A first pace (e.g. a 2 volt pace) could be delivered to a first target tissue (e.g. cardiac tissue) and a second pace (e.g. a 2 volt pace) could be delivered to a second target tissue (e.g. cardiac tissue) within the same cardiac cycle. In this example, the capture achieved the same result as the single pace delivered at 5 volts but less total energy (i.e. 4 volts) was used compared to the 5 volts for a single pace.

Another embodiment of the disclosure contemplates using a precharge and a pace. A first pace (e.g. a 1 volt pace) could be delivered to a first target tissue (e.g. cardiac tissue) and a second pace (e.g. a 1 volt pace) could be delivered to a second target tissue (e.g. cardiac tissue) within the same cardiac cycle. In this example, the capture achieved the same result as the single pace delivered at 5 volts but less total energy (i.e. 2 volts) was used compared to the 5 volts for a single pace. Energy is conserved by not delivering a typical charge (e.g. 5 volts) to tissue.

In another embodiment of the disclosure, a precharge and a pace are employed. A first pace (e.g. a pace in the range of 1 volt to about 2 volts) could be delivered to a first target tissue (e.g. cardiac tissue) and a second pace (e.g. a pace in the range of 1 volt to about 2 volts) could be delivered to a second target tissue (e.g. cardiac tissue) within the same cardiac cycle. In this example, the first pace and the second pace are different voltages but achieves the same or similar capture as the 5 volt pace. In addition, energy is conserved by not delivering a full 5 volts to tissue.

One or more embodiments, relates using the capture described herein to automatically select or present on a graphical user interface on a computer (e.g. programmer the optimal vectors. Optimal vectors employ minimum thresholds to capture and/or avoid undesirable phrenic nerve stimulation. In one or more embodiments, vector combinations (i.e. first pacing vector, second pacing vector) are selected to approximate normal contraction mechanics. In one or more other embodiments, vector combinations (i.e. first pacing vector, second pacing vector) are selected to optimize pacing sequences based on stroke volume or ejection fraction.

Skilled artisans will appreciate that the methods described herein are not limited to predetermined recharging time periods as taught by conventional devices. The set of recharge requirements described herein provide greater flexibility to implantable medical devices and may extend battery life.

The flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing circuitry to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Additionally, in the flow charts presented herein, it is recognized that all blocks shown may not be performed in some embodiments or may be performed in a different order than the order shown. Furthermore, operations described in conjunction with separate flow charts presented herein may be combined in any combination to successfully achieve the result of selecting multiple pacing sites along a heart chamber and selecting an energy efficient manner for delivering the multi-site pacing.

In addition, pacing pulses may be applied to multiple sites in the same or differing heart chambers to treat other cardiac conditions, e.g., treating tachyarrhythmias by closely spaced pacing pulses delivered through a plurality of somewhat overlapping or non-overlapping pacing paths. In one or more other embodiments, the selection of the ring or case electrode can be determined by the programmed pace polarity for each chamber of the heart.

In one or more other embodiments, an integrated diagnostics risk score algorithm can be used to compute a risk score of a prospective heart failure event (HFE), and, in response to the calculated risk HFE, implement multisite pacing for a pre-specified period of time or until a precondition is met. A HFE occurs when one of two criteria are present. First, a HFE is declared when a patient is admitted to the hospital for worsening HF. Second, the patient received Intravenous HF therapy (e.g. IV diuretics/vasodilators) or ultrafiltration at any location (e.g. Emergency Department, ambulance, observation unit of a medical unit, Urgent Care, HF/Cardiology Clinic, patient's home etc.)

In response to the risk score for the HFE, multisite pacing can be performed that examines trends for a HFE in the next 30 days. A different therapy (e.g. multisite pacing) can be automatically implemented by the IMD processor during a heart failure exacerbation. Alternatively, the IMD can receive a HFE risk status that causes the automatic implementation of multisite pacing.

In one or more other embodiments, multisite pacing can be automatically implemented during a HFE exacerbation. Once the exacerbation is resolved, the electrical stimulation can return to regular pacing that was previously specified for that patient. For example, suppose the medical personnel believe a patient can benefit from multisite pacing but are also concerned about the drain on the battery for the implantable medical device. The pacing therapy could be switched by switching circuitry 58 to the multisite pacing therapy believed to be more efficacious during the exacerbation and then switched back to the regular pacing therapy once the exacerbation has run its course.

Figure 17:
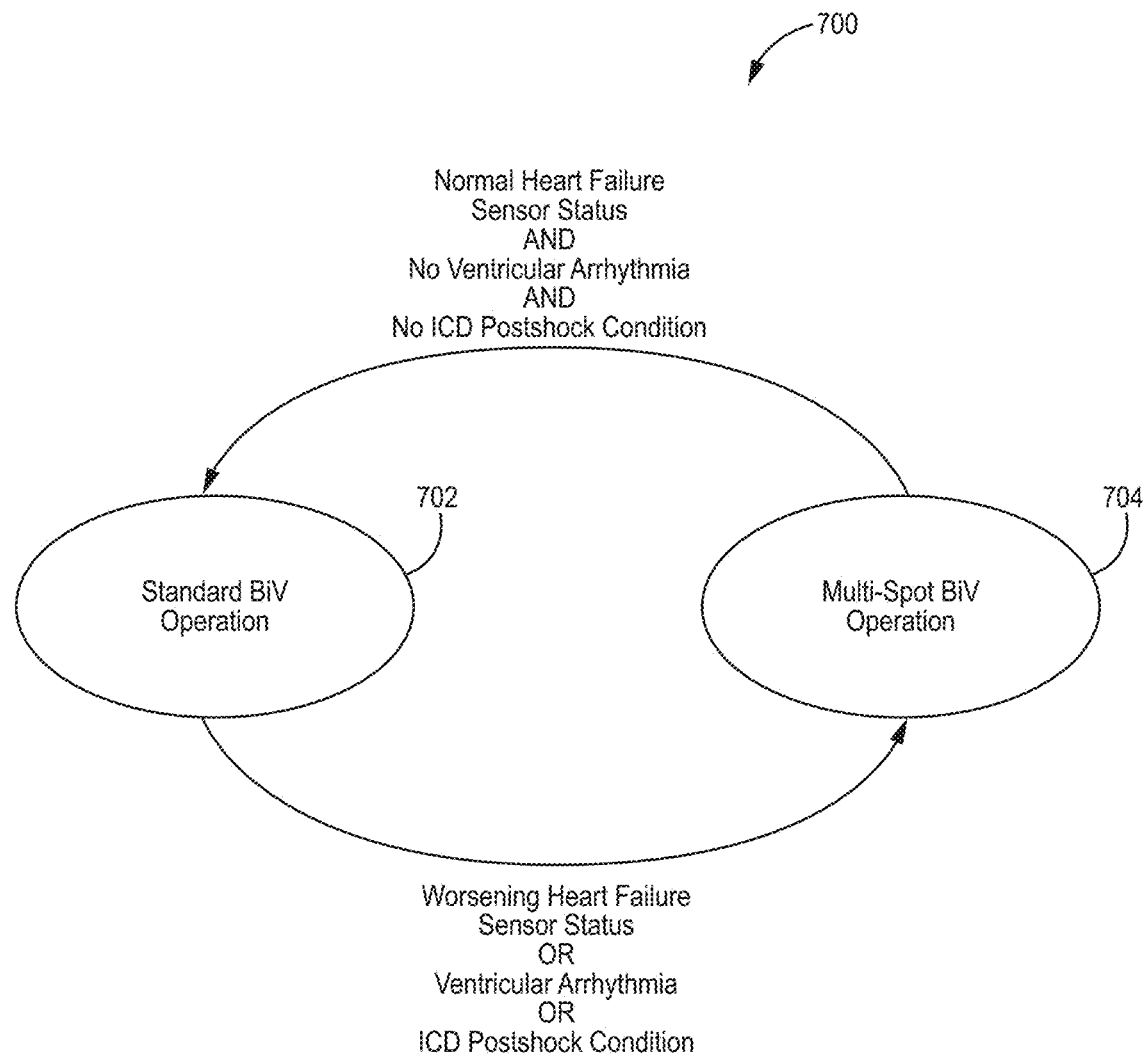
FIG. 17 is diagram that generally shows switching between delivering electrical stimuli at a single pacing site to multisite pacing during a single cardiac cycle.

FIG. 17 is a flow diagram that depicts method 700 in which IMD 10 automatically switches between delivering conventional cardiac resynchronization therapy (CRT) (i.e. biventricular or fusion pacing delivered to a single left ventricular pacing site (LV site)) and multisite pacing of the LV during a single cardiac cycle. Switching between conventional CRT to multisite pacing occurs in response to the processing circuitry 54 detecting a triggering condition (e.g. switching mode condition to switch from conventional CRT to multiple point pacing). At block 702, for example, the IMD 10 employs conventional CRT pacing such as biventricular pacing. Typically, conventional CRT is delivered when a congestive heart failure patient is experiencing a normal heart failure sensor status. For example, the processing circuitry 54 can be configured to evaluate one or more parameters to determine whether a patient is exhibiting worsening HF such that a prospective heart failure event (HFE) may occur in the near future (e.g. next 30 days). Exemplary parameters useful in determining a HFE can include an increasing trend of high or low night heart rate, decreasing trend of low heart rate variability, decreasing trend of patient physical activity, or other suitable parameters.

Additionally and/or alternatively, the therapy delivery circuit 50 continues to cause conventional CRT to be delivered to cardiac tissue after processing circuitry 54 (or programmer in communication with IMD 10) determines ventricular arrhythmia is not present and/or is not detected by sensing circuitry 60. Moreover, therapy delivery circuit 50 continues to cause CRT pacing to be delivered to cardiac tissue after processing circuitry 54 determines the patient has not experienced a ICD post-shock condition. In contrast, patients experiencing a triggering condition, can cause the IMD 10 to automatically switch to multisite pacing. A triggering condition occurs when the IMD 10 sensing circuitry 60 acquires data from electrodes that causes processing circuitry 54 to detect one of worsening heart failure sensor status, ventricular arrhythmia, or a ICD post-shock condition.

Figure 18:
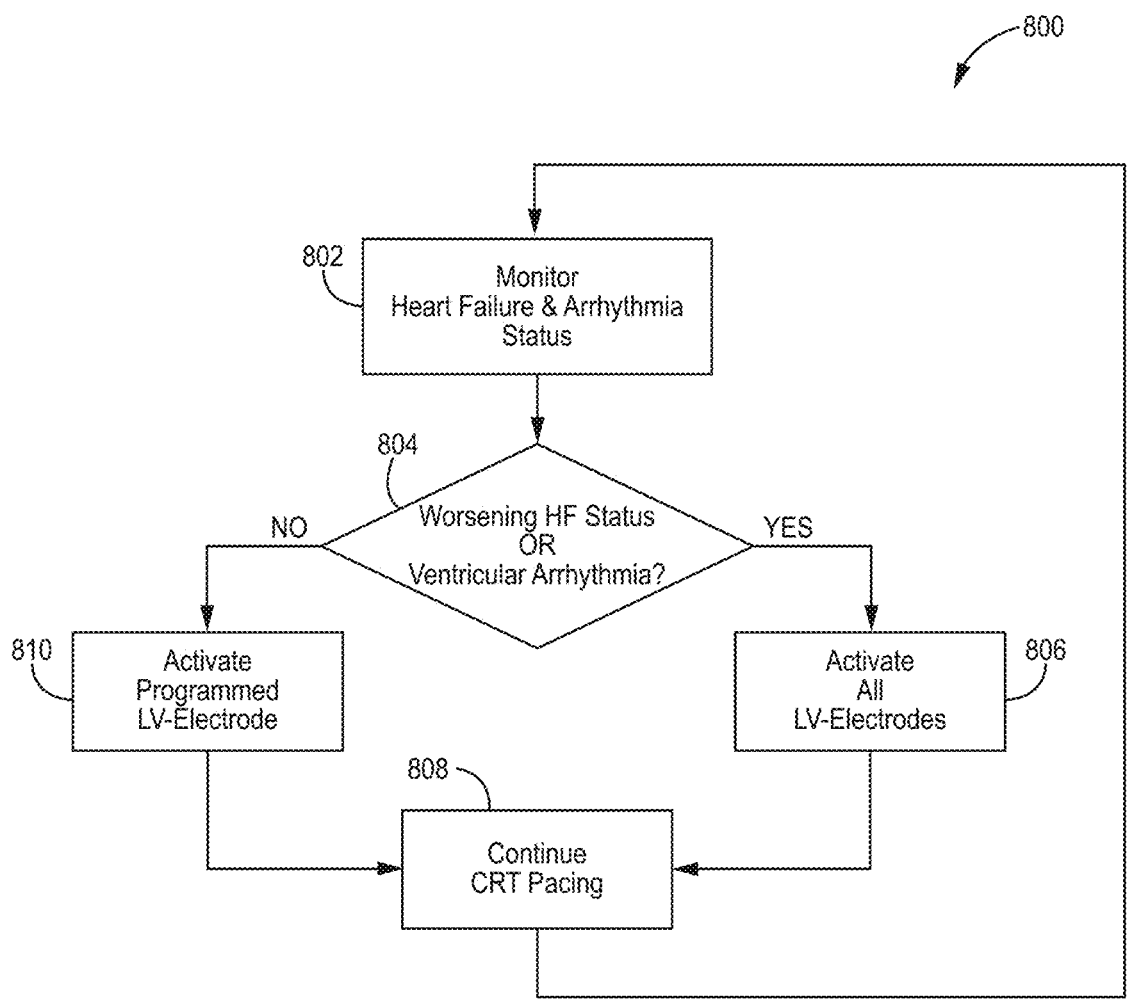
FIG. 18 is diagram that generally depicts steps involved in switching between delivering electrical stimuli at a single pacing site to multisite pacing during a single cardiac cycle.

FIG. 18 is a flow diagram that depicts method 800 performed by IMD 10. Method 800 is similar to method 700 but provides more detailed steps to achieve a closed loop system to automatically switch from conventional CRT to multisite pacing.

Method 800 begins at block 802 in which heart activity is acquired by IMD 10 via sensing circuitry 60 receiving signals from electrode(s) located in, on or near the cardiac tissue (e.g. left ventricle, right ventricle, right atrium, left atrium). Exemplary data that may be directly used to determine whether congestive heart failure is worsening is varied. The data can be directly acquired from electrodes associated with an implantable medical device 10. In addition or alternatively, data can be acquired from other implantable medical devices in communication with implantable medical device 10. Exemplary implantable medical devices in communication implantable medical device 10 include implantable recording devices such as LINQ™ commercially available from Medtronic, Inc. located Minneapolis, Minn. In addition or alternatively, data can be obtained from devices that include exterior electrodes (i.e. exterior to a patient's body such as skin electrodes etc.). Data that is acquired from devices other than IMD 10 can be communicated to implantable medical device 10 so that the processing circuit 54 can determine with a triggering condition has occurred to automatically switch from conventional CRT (i.e. deliver single site pacing) to multisite pacing. Alternatively, a computing device exterior to the patient's body can acquire the implantable medical device data and determine whether a triggering condition is present to switch from conventional CRT to multisite pacing.

Data that includes heart rate, heart rate variability, fluid status, tissue edema, minute ventilation, activity, filling pressure, oxygenation, temperature etc.

Heart rate is the speed of the heartbeat measured by the number of contractions (i.e. beats) of the heart per minute (bpm). The heart rate may be too fast, referred to as tachycardia, or too slow, referred to as bradycardia.

Reduced variability in the patient's heart rate may help identify heart failure decompensation. IMD 10 is configured to measure each atrial interval and calculates the median atrial interval every 5 min. IMD 10 can then calculates a variability value (in ms) for each day.

Fluid Status data measures the patient's thoracic impedance. The RVcoil to Can electrodes form a pathway that passes through the tissue in the thoracic cavity. Increases in thoracic fluid cause a decrease in impedance for this pathway. Decreases in thoracic fluid cause an increase in impedance for this pathway. Edema is accumulation of excessive fluid in the tissues.

Respiratory minute volume (or minute ventilation or minute volume) is the volume of gas inhaled (inhaled minute volume) or exhaled (exhaled minute volume) from a person's lungs per minute.

Filling pressure is the pressure in the ventricle as it fills with blood; ordinarily equivalent to the mean atrial pressure when there is no AV valvular gradient. Examples of data that may be acquired relative to IMD 10 is described with respect to U.S. Pat. No. 7,027,866 B2, U.S. Pat. No. 8,271,072 and assigned to the assignee of the present invention, the disclosures of which are incorporated by reference in their entirety herein. As previously data may also be acquired non-invasively via non-implantable electrodes (e.g. electrodes located on wearable items such as watches (e.g. Garmin™ FORERUNNER™, FITBIT™, Apple iWatch™ etc.) and/or an ECG belt or vest to help determine whether a congestive HF patient's condition is worsening. Exemplary data that may be acquired from watches are designed to track activity (e.g. walking, running, swimming, cycling, skiing, rowing, surfing, hiking, rock climbing, tennis, sleeping and/or movement while sleeping, etc.) that may be helpful to determine whether the patient activity has dramatically decreased over a period of time (e.g. short period of time e.g. 1 month etc.) or gradual decreased activity that is statistically significant over a longer period of time (e.g. 1 year etc.). Exemplary health data from non-implantable electrodes (e.g. watch) comprises $VO_2$ maximum, heart rate, heart rate variability, all day heart rate, all day stress, data displaying trend of heart rate over a predetermined time (up to 1 hour, 1 day, 1 week, 1 month, 1 year etc.) Other data may comprise weight that is automatically and wirelessly transferred from a weight scale, referred to as GARMIN™ Index Weight Scale, commercially available from GARMIN™ located in Olathe Kansas over BLUETOOTH™ to a processor circuitry located in a personal digital assistant (e.g. cell phone) or a computer. In addition, data may be acquired from ECG belts or vests. Examples of data that may be acquired relative to an ECG belt or vest is described with respect to U.S. Pat. No. 9,132,274 B2, U.S. Pat. No. 9,278,219 and assigned to the assignee of the present invention, the disclosures of which are incorporated by reference in their entirety herein. Data acquired from non-implantable sensors may be stored into memory of the non-implantable device (e.g. watch, PDA, etc.) and/or wirelessly transmitted over BLUETOOTH™ to a server that saves date into memory.

The data sensed from implantable electrode(s) is stored into memory 82 of the IMD 10 that can be wirelessly transferred to a programmer and/or a personal digital assistant. Exemplary information acquired from sensed data (e.g. EGMs) include QRS duration, R-wave timing, pacing-RV (or LV) sensing, and/or VV interval. Pacing-RV (or LV) sensing means the time interval from pacing (or pacing artifact) to the RV (or LV) sensing. Data acquired from other implantable medical devices or devices exterior to IMD 10 can be communicated to IMD 10 and stored into memory of IMD 10. Alternatively, a programmer or computer can acquire data from IMD 10. The programmer or a computer can process the data acquired from devices other IMD 10. The programmer or the computer can signal IMD 10 to switch from conventional CRT to multisite pacing.

At decision block 804, the processor 54 of the IMD 10 uses the data, acquired from the sensed heart activity (e.g. recording of EGMs etc.) in block 802, to determine whether HF condition(s) are worsening. An example of data that may indicate whether congestive heart failure is worsening may be seen with respect to US 2016-0361026 A1, entitled "METHOD AND APPARATUS FOR MONITORING TISSUE FLUID CONTENT FOR USE IN AN IMPLANTABLE CARDIAC DEVICE" filed, Feb. 20, 2012, U.S. Pat. No. 9,247,883 B2, entitled "Detecting Worsening Heart Failure Based On Fluid Accumulation With Respiratory Confirmation" and assigned to the assignee of the present invention, the disclosure of which are incorporated by reference in their entirety herein.

Data can be tracked over time to show trends. Data trends can be provided up to a certain amount of time (e.g. 14 months or more etc.) of clinically significant patient data. Exemplary data trends includes the frequency of arrhythmias, physical activity, heart rates, and implantable medical device therapies. An atrial arrhythmia trend and a histogram of ventricular rate during atrial tachycardia or atrial fibrillation (AT/AF) can be provided in IMD 10. Medtronic Insertable Cardiac Monitors (ICM) (e.g. REVEAL™) include trends in the occurrence of arrhythmias and symptoms, the amount of physical activity and heart rate variability. The Cardiac Compass trends are based on data and measurements collected daily. Data storage for Cardiac Compass trends is automatically performed. The IMD 10 begins storing data after the IMD 10 is implanted in the patient. Each day thereafter, the device stores a set of Cardiac Compass trend data. Storage of data into memory continues until the 14-month storage capacity is filled. At that point, the oldest stored data can be overwritten with new data. An analysis of clinical information collected over a long term can help clinicians follow changes in a patient's condition and correlate these changes with variations in device programming, medication, patient activity, or symptoms.

If a patient's congestive HF condition is worsening, processing circuitry 54 causes switching circuitry 58 to activate more or all of the electrodes on the pacing device(s) 10 (e.g. left heart lead, leadless pacing device(s) etc.) deliver pacing to the tissue at block 806.

Another determination can be made by processing circuitry 54 as to whether the patient is experiencing ventricular arrhythmia. Ventricular arrhythmias include ventricular tachycardia and ventricular fibrillation. Arrhythmias can comprise abnormal rapid heart rhythms (i.e. arrhythmias) that originate in the lower chambers of the heart (the ventricles).

Ventricular dyssynchrony can cause ineffective ventricular filling and contraction, leading to worsening of heart failure symptoms that can result in reduced stroke volume and, consequently, reduced blood flow to the body. Cardiac resynchronization therapy (CRT) treats ventricular dyssynchrony by providing coordinated paces to both the left and right ventricles. Successful resynchronization of left and right ventricles improves the efficiency of each contraction, thus increasing cardiac output.

If processing circuitry 60 determines a patient's congestive HF condition is not worsening at block 804, IMD 10 processing circuitry 60 continues to block 810 and activates the LV electrode that is selected to pace cardiac tissue. Selection of the LV electrode to pace cardiac tissue can be based upon optimal activations times that are responsive to pacing stimuli delivered by IMD 10. U.S. Pat. No. 8,750,998 B1 provides an example way in which optimal electrode(s) can be selected to pace cardiac tissue.

At block 808, CRT pacing is delivered using the selected electrode(s) located on a medical electrical lead (e.g. ATTAIN PERFORMA™). For example, a single pacing vector is employed to pace cardiac tissue when continuing from block 810.

Figure 19:
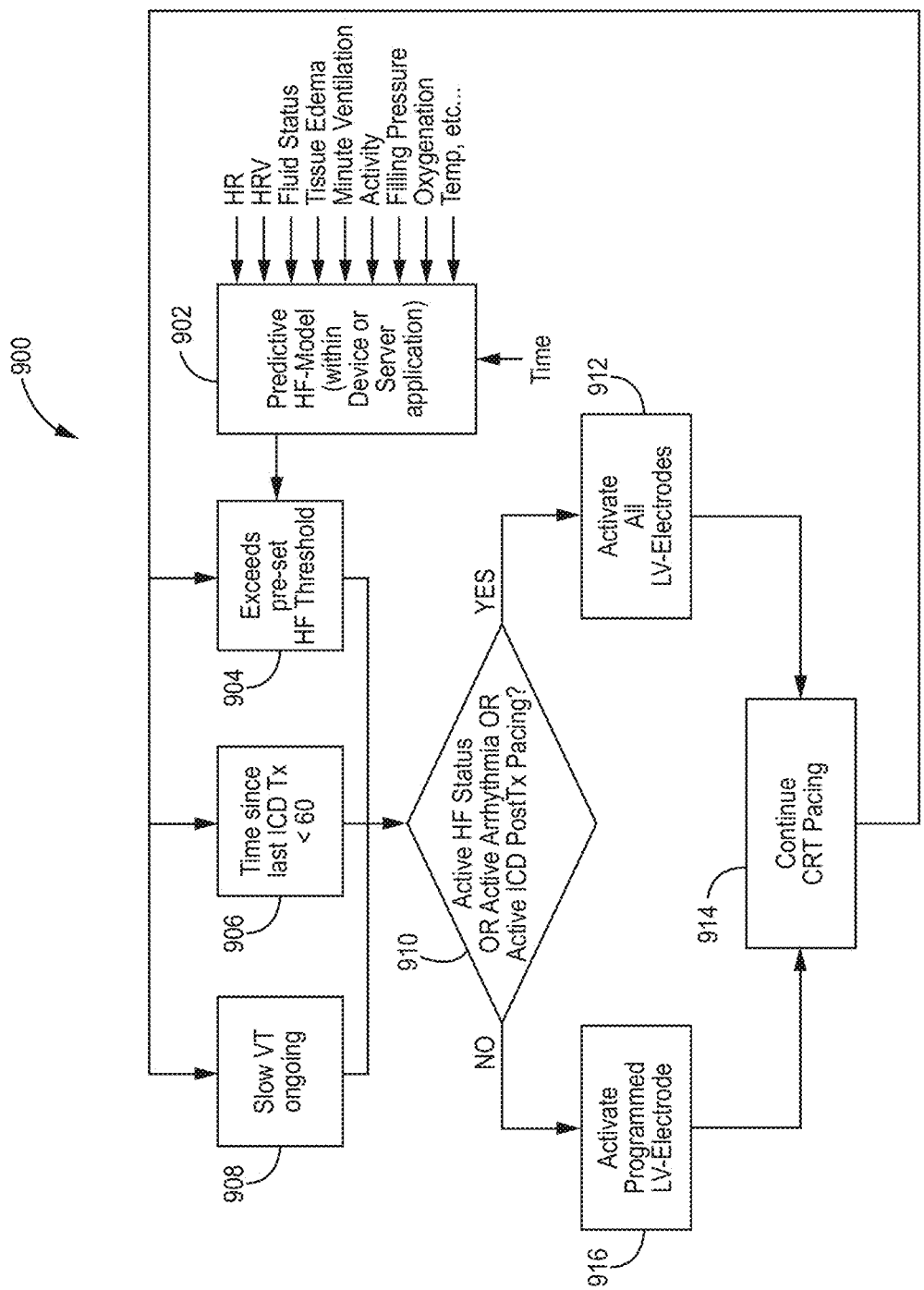
FIG. 19 is diagram that generally depicts steps involved in switching between delivering electrical stimuli at a single pacing site to multisite pacing during a single cardiac cycle.

FIG. 19 depicts a flow diagram of method 900 in which processing circuitry 60 of IMD 10 automatically causes the signal generator to generate pacing pulses delivered to cardiac tissue through using a single pacing vector to pacing with a set or all of pacing vectors along a lead (e.g. left ventricular lead) disposed along the cardiac tissue (e.g. ventricle (i.e. LV, and/or RV), atria (i.e. LA, RA)). At block 902, a set of data is acquired through sensing data from LV electrodes on the lead coupled to cardiac tissue. The data can be acquired from the IMD 10, as shown, for example, in FIG. 1. Sensed data can also be acquired via wearable sensors or from a hospital visit. Exemplary data acquired in block 902 includes heart rate, heart rate variability, fluid status, tissue edema, minute ventilation, activity, filling pressure, oxygenation, and/or temperature etc.

Data input from blocks 904-908 form block 802 of FIG. 18. At block 904, the processing circuitry (processor 54, programmer, and/or server processor) determines whether a congestive HF threshold has been crossed. Crossing a threshold can involve exceeding a threshold that causes a response to be triggered. For example, when a patient's heart rate exceeds a pre-determined level (e.g. 200 beats per minute), the IMD 10 may be configured to automatically signal an alert to the patient and/or physician. Crossing a threshold can also include when electrolyte (e.g. potassium, magnesium, sodium etc.) levels are determined, by IMD 10, to be too low for a patient. Electrolyte data can be acquired in a variety of ways including through a sensor coupled to the implantable medical device.

At block 906, the time in which ICD therapy is delivered is less than a pre-specified interval because it is desirable to determine whether the ICD therapy is effective. For example, ICD therapy (e.g. defibrillation) may be 1 minute (e.g. 60 seconds). Typically, the pre-specified interval is less than 15 minutes.

At block 908, a determination is made, by processing circuitry 54 using data sensed from electrodes coupled to cardiac tissue, that slow ventricular tachycardia (VT) (<148 bpm) is present. Slow VT can be efficiently and safely terminated by anti-tachycardia (ATP) pacing.

At block 910, a determination is made by processing circuitry 54 as to whether the patient is experiencing congestive HF status.

Yet another determination is made by processing circuitry 54 as to whether the patient is experiencing an active arrhythmia.

Still yet another determination is made by processing circuitry 54 as to whether an active ICD post therapy pacing.

The NO path from block 910 continues to block 916 in a LV electrode is programmed to deliver pacing pules to cardiac tissue.

The YES path from block 910 continues to block 912 in which all or a portion of all of the pacing electrodes are activated by the switching circuit to deliver pacing pulses to the cardiac tissue (i.e. LV). Thereafter, CRT pacing is continued at block 914.

Figure 20:
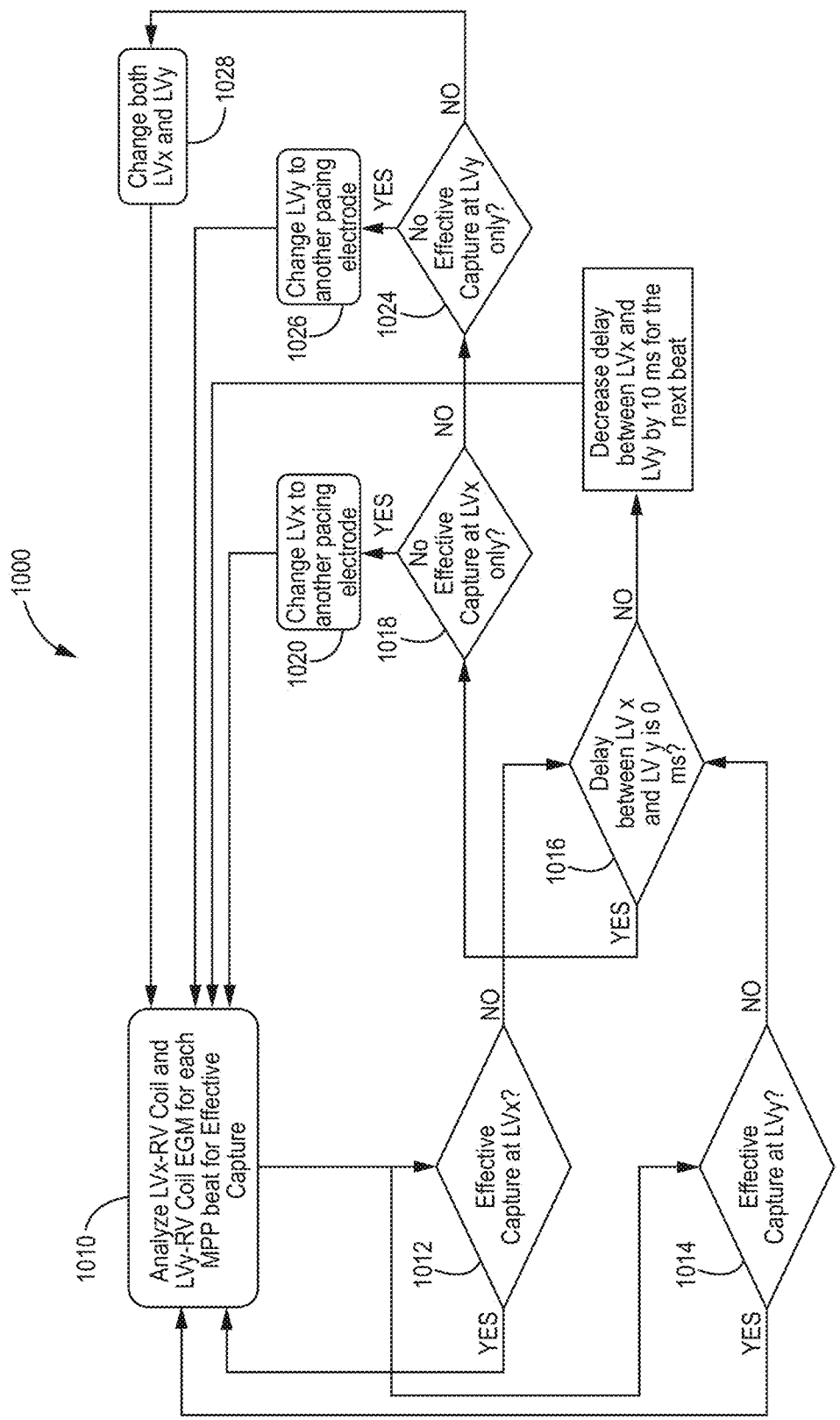
FIG. 20 is a flow diagram that is implemented by an implantable medical device that detects ineffective capture and, in response, automatically switches between pacing a single site to delivering multisite pacing along a single chamber (e.g. left ventricle etc.) during a single cardiac cycle.

FIG. 20 is a flow diagram that is implemented, in a closed loop, by an implantable medical device 10 that detects ineffective capture and, in response, IMD 10 is configured to automatically switch between pacing a single site to delivering multisite pacing along a single chamber (e.g. left ventricle etc.) during a single cardiac cycle. Switching between single and multisite pacing is performed in a closed loop system by IMD 10. Method 1000 is further configured to monitor sensed signals using the sensing circuitry 60 in response to the pacing stimuli (e.g. pacing pulses) generated by the therapy delivery circuitry 50. In response to the monitored (or sensed) electrical signals, the processing circuitry 54 of IMD 10 can modify timing of the pacing stimuli from one or more of the pacing electrodes. The timing of the pacing stimuli is modified or controlled based upon whether effective capture is achieved by the pacing stimuli delivered from the pacing electrode to the cardiac tissue. For example, the timing of the pacing pulses can be adjusted to be delivered earlier if effective capture is not occurring one or more LV electrodes. Alternatively, if effective capture is occurring, the timing can be increased.

Method 1000 uses a multielectrode implantable medical device 10. The multi-electrode device (e.g. 2 electrodes, 4 electrodes etc. on a quadripolar lead, or N electrodes on an implantable device (that includes a lead) in which N is an integer up to 16) is to ensure that the window for analysis for effective capture is actually starting on the first pacing event. The first pacing event can include simultaneous pacing events or sequential pacing events. In one embodiment, a window is configured to capture sequential of activation or sequential delays.

Method 1000 begins at block 1010 in which signals are sensed via non-pacing electrodes on or associated with the implantable medical device 10. Cardiac EGM signals (either analog sensed event signals or digitized signals or both) are acquired by processor 54 for detecting physiological events, such as detecting and discriminating cardiac arrhythmias. Left ventricular electrode, designated as x, being one of the electrodes on a quadripolar left ventricular lead to RV coil electrode (LVx-RV Coil) and left ventricular electrode, designated as y, being one of the electrodes on a quadripolar left ventricular lead to RV coil electrode (LVy-RV Coil) signals are sensed by electrodes and acquired by sensing circuitry 60. X is the designation for one electrode and Y is the designation for another electrode on the left ventricular quadripolar lead. A sensing amplifier for LV sensing is not needed. EGM channels record electrical activity between these electrodes. Processing circuitry 54 analyzes the sensed signals for effective capture. The firmware can then execute algorithm(s) to cause the processing circuitry 54 to modify parameters in a closed loop fashion.

Block 1010 also causes processing circuitry 54 to analyze LVx-RV coil signal and LVy-RV coil signal for each multipoint beat for effective capture. As previously stated, effective capture for each beat can be analyzed using U.S. Pat. No. 8,750,998, incorporated by reference in its entirety herein.

At decision block 1012, a determination is made by processing circuitry 54 as to whether effective capture occurred at the tissue site where the LVx electrode is located. The YES path from decision block 1012 returns to block 1010 to continue monitoring signals by processing circuitry 54. The NO path from block 1012 continues to decision block 1016 in which a determination is made by processing circuitry 54 as to whether a delay between LVx and LVy is de minimis (e.g. 0 ms or about 0 ms). The NO path from decision block 1016 continues to block 1022 in which the delay is decreased by processing circuitry 54 between LVx and LVy by a predetermined amount (e.g. 5 ms, 10 ms, any time up to 15 ms) for the next beat. processing circuitry 54 signals the timing circuit to update timing between LVx and LVy. After the delay has been decreased, the logic returns to sensing and analyzing signals at block 1010, as previously described.

Simultaneous to effective capture at LVx being evaluated at decision block 1012, effective capture is also evaluated at LVy at decision block 1014. At block 1014, if effective capture occurs at LVy, the YES path returns to block 1010 to continue monitoring and analyzing signals as previously described. The NO path from block 1014 continues to block 1016 to determine whether the delay between LVx and LVy is 0 ms. The NO path from block 1016 continues to block 1012 in which the delay is decreased for the next beat, as previously described, and then returns to monitoring and analyzing sensed signals at block 1010.

Returning to block 1016, if the delay between LVx and LVy is 0 ms, the YES path continues to decision block 1018 in which processing circuitry 54 determines whether effective capture only occurred at LVx only. The YES path from block 1018 continues to block 1020 in which the pacing circuitry 54 automatically changes LVx to another pacing electrode. For example, LVx can be changed to another pacing electrode along the LV lead. After LVx has been changed to another pacing electrode, the IMD 10 returns to block 1010 to continue monitoring and analyzing sensed signals.

If a determination at decision block 1018 indicates effective capture is occurring at block 1018, the NO path continues to decision block 1024 so that a determination can be made by processing circuitry 54 as to whether effective capture is occurring at LVy only. The YES path from decision block 1024 continues to block 1026 in which LVy is changes to another pacing electrode. After LVy is changed to another pacing electrode along, for example, the LV lead, IMD 10 continues to sense and analyze the sensed signals for effective capture at block 1010.

The NO path from block 1024 requires that both LVx and LVy be changed to other pacing electrodes. IMD 10 continues to sense signals at block 101.

The delay between LVx and LVy can range between 0-4 ms. Simultaneous pacing can be defined as occurring between 0-0.4 ms in one embodiment.

In another embodiment to FIG. 20, a flowchart would be exactly the same as FIG. 20 except box 1016 is replaced such that the switch to a different electrode set occurs in response to the delay between the delivered LV pacing pulses being less than a preset duration "x", which will typically be a few milliseconds or less, e.g. 0 to 5 ms.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs. The term "processor" or "processing circuitry" may generally refer to any of the foregoing logic circuitry, alone or in combination with other logic circuitry, or any other equivalent circuitry.

It will also be appreciated that the stimulation energy may be other than a pacing pulse, and that the stimulation path may constitute other living body tissue stimulated at multiple sites in a sequential fashion, e.g., nerve, bladder, sphincter, brain, and other organs or muscle groups. The problems of recharging any reactive living body tissue stimulation path to enable closely spaced delivery of stimulation pulse energy can be addressed in the manner described above.

While the pace current can be configured to travel from the anode to the cathode, skilled artisans appreciate that the circuit diagram could be configured to cause the pace current to travel from the cathode to the anode.

The following paragraphs enumerated consecutively from 1-37 sprovide for various aspects of the present disclosure. In one embodiment, the present disclosure provides a first embodiment of a pacing device comprising a set of electrodes including a first ventricular electrode and a second ventricular electrode, spatially separated from one another and all coupled to an implantable pulse generator.

Embodiment 1 is a pacing device comprising:
a set of electrodes including first and second left ventricular electrodes spatially separated from one another and a right ventricular electrode, all coupled to an implantable pulse generator; and
a processing circuit coupled to the implantable pulse generator, the processing circuit configured to determine whether a prospective heart failure condition has occurred and if so to trigger the pulse generator to switch from a first pacing mode to a second pacing mode, the first pacing mode comprising delivering only a first pacing pulse to a left ventricle (LV) and thereafter delivering an RV pacing pulse to the right ventricular electrode within a single cardiac cycle and the second pacing mode comprising delivering first and a second pacing pulses to the LV and thereafter delivering an RV pacing pulse to the right ventricular electrode within a single cardiac cycle.

Embodiment 2 is a pacing device of embodiment 1 wherein the processing circuit is configured to receive parameters regarding at least one of: heart rate, heart rate variability, fluid status, tissue edema, minute ventilation, activity, electrolyte level, filling pressure, oxygenation, and/or temperature and to determine whether the at least one parameter exceeds a set threshold and wherein exceeding the set threshold comprises a determination that the prospective heart failure condition has occurred.

Embodiment 3 is the pacing device of any of embodiments 1-2 wherein the processing circuit is configured to receive arrhythmia data sensed from one or more electrodes from the set of electrodes.

Embodiment 4 is the pacing device of any of embodiments 1-3 wherein the processing circuit is configured to receive ICD post-shock data.

Embodiment 5 is the pacing device of any of embodiments 1-4 wherein the implantable pulse generator generates signal pulses to two or more left ventricular electrodes, disposed on a lead, during the same cardiac cycle.

Embodiment 6 is the pacing device of any of embodiments 1-5 wherein the implantable pulse generator generates signal pulses to up to four left ventricular electrodes, disposed on a lead, during the same cardiac cycle.

Embodiment 7 is the pacing device of any of embodiments 1-6 wherein the processing circuit is configured to receive worsening heart failure condition data.

Embodiment 8 is a pacing device comprising:
a set of electrodes including first and second left ventricular electrodes spatially separated from one another and a right ventricular electrode, all coupled to an implantable pulse generator; and
a processing circuit coupled to the implantable pulse generator, the processing circuit configured to determine whether a ventricular tachycardia is occurring and if so to trigger the pulse generator to switch from a first pacing mode to a second pacing mode, the first pacing mode comprising delivering only a first pacing pulse to a left ventricle (LV) and thereafter delivering an RV pacing pulse to the right ventricular electrode within a single cardiac cycle and the second pacing mode comprising delivering first and a second pacing pulses to the LV and thereafter delivering an RV pacing pulse to the right ventricular electrode within a single cardiac cycle.

Embodiment 9 is a pacing device comprising:
a set of electrodes including first and second left ventricular electrodes spatially separated from one another and a right ventricular electrode, all coupled to an implantable pulse generator; and
a processing circuit coupled to the implantable pulse generator, the processing circuit configured to determine whether less than a defined interval of time has elapsed since delivery of a defibrillation pulse from an implantable cardiac defibrillator and if so, to trigger the pulse generator to switch from a first pacing mode to a second pacing mode, the first pacing mode comprising delivering only a first pacing pulse to a left ventricle (LV) and thereafter delivering an RV pacing pulse to the right ventricular electrode within a single cardiac cycle and the second pacing mode comprising delivering first and a second pacing pulses to the LV and thereafter delivering an RV pacing pulse to the right ventricular electrode within a single cardiac cycle.

Embodiment 10 is a pacing device comprising:
a set of electrodes including first, second, third, and fourth left ventricular (LV) electrodes spatially separated from one another and all coupled to an implantable pulse generator,
a processing circuit coupled to the implantable pulse generator, the processing circuit configured to:
a) cause the pulse generator to deliver pacing in a pacing mode comprising delivering first pacing and second pacing pulses to a left ventricle (LV) within a single cardiac cycle using the first and second LV electrodes;
b) to determine duration of a delay between the first and second pacing pulses; and
c) to determine whether capture has been lost at one or both of the first and second LV electrodes and if so to trigger the pulse generator to modify the pacing mode in response to the determined loss of capture, wherein the modification to the pacing mode comprises;
  i) when the determined delay between the first and second pacing pulses is greater than a preset duration, subsequently delivering following pacing pulses to the left ventricle (LV) using the first and second LV electrodes separated by a delay different from the determined duration; and ii. when the determined delay between the first and second pacing pulses is less than or equal to the preset duration; subsequently delivering following pacing pulses to the left ventricle using at least one of the third and fourth LV electrodes.

Embodiment 11 is a pacing device according to embodiment 10 wherein:

when the determined delay between the first and second pacing pulses is less than or equal to the preset duration and capture is lost at only the first LV electrode, the following pacing pulses are delivered to the left ventricle using the second and third LV electrodes.

Embodiment 12 is a pacing device according to any of embodiments 10-11 wherein:

when the determined delay between the first and second pacing pulses is less than or equal to the preset duration and capture is lost at both the first and second LV electrodes, LV electrode, the following pacing pulses are delivered to the left ventricle using the third and fourth LV electrodes.

Embodiment 13 is a pacing device according to any of embodiments 10-12 wherein the preset duration is zero.

Embodiment 14 is a pacing device according to of any of embodiments 10-13 wherein the delay different from the determined duration is a delay less than the determined duration.

Embodiment 15 is a method comprising:

determining, with an implantable medical device, whether a ventricular tachycardia is occurring, and if so, triggering a pulse generator to switch from a first pacing mode to a second pacing mode, the first pacing mode comprising delivering only a first pacing pulse to a left ventricle (LV) and thereafter delivering an RV pacing pulse to a right ventricular electrode within a single cardiac cycle and the second pacing mode comprising delivering first and a second pacing pulses to a LV and thereafter delivering an RV pacing pulse to the right ventricular electrode within a single cardiac cycle.

Embodiment 16 is a method comprising:

determining whether less than a defined interval of time has elapsed since delivery of a defibrillation pulse from an implantable cardiac defibrillator and if so, triggering a pulse generator to switch from a first pacing mode to a second pacing mode, the first pacing mode comprising:

delivering only a first pacing pulse to a left ventricle (LV) and thereafter delivering an RV pacing pulse to the right ventricular electrode within a single cardiac cycle and the second pacing mode comprising delivering first and a second pacing pulses to the LV and, thereafter delivering an RV pacing pulse to the right ventricular electrode within a single cardiac cycle.

Embodiment 17 is a method comprising:

a) causing a pulse generator to deliver pacing in a pacing mode comprising delivering first pacing and second pacing pulses to a left ventricle (LV) within a single cardiac cycle using the first and second LV electrodes;

b) determining duration of a delay between the first and second pacing pulses; and c) determining whether capture has been lost at one or both of the first and second LV electrodes and if so to trigger the pulse generator to modify the pacing mode in response to the determined loss of capture, wherein the modification to the pacing mode comprises;

i) when the determined delay between the first and second pacing pulses is greater than a preset duration, subsequently delivering following pacing pulses to the left ventricle (LV) using the first and second LV electrodes separated by a delay different from the determined duration; and ii. when the determined delay between the first and second pacing pulses is less than or equal to the preset duration; subsequently delivering following pacing pulses to the left ventricle using at least one of the third and fourth LV electrodes.

Embodiment 18 is a method according to embodiment 17 wherein:

when the determined delay between the first and second pacing pulses is less than or equal to the preset duration and capture is lost at only the first LV electrode, the following pacing pulses are delivered to the left ventricle using the second and third LV electrodes.

Embodiment 19 is a method according to any of embodiments 17-18 wherein:

when the determined delay between the first and second pacing pulses is less than or equal to the preset duration and capture is lost at both the first and second LV electrodes, LV electrode, the following pacing pulses are delivered to the left ventricle using the third and fourth LV electrodes.

Embodiment 20 is a method according to any embodiments 17-19 wherein the preset duration is zero.

Embodiment 21 is a method according to any of embodiments 17-20 wherein the delay different from the determined duration is a delay less than the determined duration.

Other examples include systems comprising means for performing any of the methods described herein.

Other examples include computer-readable media comprising instructions that, when executed by processing circuitry of a medical device system, cause the processing circuitry to perform any of the methods described herein.

Thus, an apparatus and method for controlling multi-site pacing have been presented in the foregoing description with reference to specific embodiments. It is appreciated that various modifications to the referenced embodiments may be made without departing from the scope of the disclosure as set forth in the following claims.

The invention claimed is:

1. A pacing device comprising:
an implantable pulse generator;
a set of electrodes including first and second left ventricular electrodes spatially separated from one another and a right ventricular electrode, all coupled to the implantable pulse generator; and
a processing circuit coupled to the implantable pulse generator, the processing circuit configured to:
determine whether a prospective heart failure condition has occurred; and
trigger the pulse generator to switch from a first single-site pacing mode to a second multi-site pacing mode in response to determination of that prospective heart failure condition has occurred, the first single-site pacing mode comprising delivering only a single left ventricle (LV) pacing pulse to a LV using one of the first and second left ventricular electrodes and thereafter delivering a right ventricle (RV) pacing pulse to a RV using the right ventricular electrode within a single cardiac cycle and the second multi-site pacing mode comprising delivering first and second LV pacing pulses to the LV using the first and second left ventricular electrodes and thereafter delivering a RV pacing pulse to the RV using the right ventricular electrode within a single cardiac cycle, wherein the second LV pacing pulse is delivered to a different location in the LV than the first LV pacing pulse.

2. The pacing device of claim 1 wherein determining whether a prospective heart failure condition has occurred comprises:
receiving at least one parameter comprising at least one of: heart rate, heart rate variability, fluid status, tissue edema, minute ventilation, activity, electrolyte level, filling pressure, oxygenation, and temperature; and
determining that the prospective heart failure condition has occurred in response to the at least one parameter exceeding a set threshold.

3. The pacing device of claim 1 wherein the processing circuit is configured to receive arrythmia data sensed from one or more electrodes from the set of electrodes.

4. The pacing device of claim 1 wherein the processing circuit is configured to receive ICD post-shock data.

5. The pacing device of claim 1 wherein the pulse generator generates signal pulses to two or more left ventricular electrodes, disposed on a lead, during the same cardiac cycle.

6. The pacing device of claim 1 wherein the pulse generator generates signal pulses to up to four left ventricular electrodes, disposed on a lead, during the same cardiac cycle.

7. The pacing device of claim 1 wherein the processing circuit is configured to receive worsening heart failure condition data.

8. The device of claim 1, wherein the processing circuit further configured to:
determination a normal health failure status; and
trigger the pulse generator to switch from the second pacing mode to the first pacing mode in response to determination of the normal health failure status.

9. A pacing device comprising:
an implantable pulse generator;
a set of electrodes including first and second left ventricular electrodes spatially separated from one another and a right ventricular electrode, all coupled to the implantable pulse generator; and
a processing circuit coupled to the implantable pulse generator, the processing circuit configured to:
determine whether a ventricular tachycardia is occurring; and
trigger the pulse generator to switch from a first single-site pacing mode to a second multi-site pacing mode in response to determination that ventricular tachycardia is occurring, the first single-site pacing mode comprising delivering only a single left ventricle (LV) pacing pulse to a LV using one of the first and second left ventricular electrodes and thereafter delivering a right ventricular (RV) pacing pulse to a RV using the right ventricular electrode within a single cardiac cycle and the second multi-site pacing mode comprising delivering first and second LV pacing pulses to the LV using the first and second left ventricular electrodes and thereafter delivering a RV pacing pulse to the RV using the right ventricular electrode within a single cardiac cycle, wherein the second LV pacing pulse is delivered to a different location in the LV than the first LV pacing pulse.

10. The device of claim 9, wherein the processing circuit further configured to trigger the pulse generator to switch from the second pacing mode to the first pacing mode in response to determination that ventricular tachycardia is not occurring.

11. A pacing device comprising:
an implantable pulse generator;
a set of electrodes including first and second left ventricular electrodes spatially separated from one another and a right ventricular electrode, all coupled to the implantable pulse generator; and
a processing circuit coupled to the implantable pulse generator, the processing circuit configured to:
determine whether less than a defined interval of time has elapsed since delivery of a defibrillation pulse from an implantable cardiac defibrillator; and
trigger the pulse generator to switch from a first single-site pacing mode to a second multi-site pacing mode in response to determination that less than the defined interval of time elapsed since delivery of the defibrillation pulse from the implantable cardiac defibrillator, the first single-site pacing mode comprising delivering only a single left ventricle (LV) pacing pulse to a LV using one of the first and second left ventricular electrodes and thereafter delivering a right ventricle (RV) pacing pulse to a RV using the right ventricular electrode within a single cardiac cycle and the second multi-site pacing mode comprising delivering first and second LV pacing pulses to the LV using the first and second left ventricular electrodes and thereafter delivering a RV pacing pulse to the RV using the right ventricular electrode within a single cardiac cycle, wherein the second LV pacing pulse is delivered to a different location in the LV than the first LV pacing pulse.

12. The device of claim 11, wherein the processing circuit further configured to trigger the pulse generator to switch from the second pacing mode to the first pacing mode in response to determination that not less than the defined interval of time elapsed since delivery of the defibrillation pulse from the implantable cardiac defibrillator.

13. A method comprising:
determining, with an implantable medical device, whether a ventricular tachycardia is occurring; and
triggering a pulse generator to switch from a first single-site pacing mode to a second multi-site pacing mode in response to determination of that ventricular tachycardia is occurring, the first single-site pacing mode comprising delivering only a single left ventricle (LV) pacing pulse to a LV and thereafter delivering a right ventricle (RV) pacing pulse to a RV using a right ventricular electrode within a single cardiac cycle and the second multi-site pacing mode comprising delivering first and second LV pacing pulses to the LV using the first and second left ventricular electrodes and thereafter delivering a RV pacing pulse to the RV using the right ventricular electrode within a single cardiac cycle, wherein the second LV pacing pulse is delivered to a different location in the LV than the first LV pacing pulse.

14. A method comprising:
determining whether less than a defined interval of time has elapsed since delivery of a defibrillation pulse from an implantable cardiac defibrillator; and
triggering a pulse generator to switch from a first single-site pacing mode to a second multi-site pacing mode in response to determination that less than the defined interval of time elapsed since delivery of the defibrillation pulse from the implantable cardiac defibrillator, the first single-site pacing mode comprising delivering only a single left ventricle (LV) pacing pulse to a LV using one of first and second left ventricular electrodes and thereafter delivering a right ventricle (RV) pacing pulse to a RV using a right ventricular electrode within a single cardiac cycle and the second multi-site pacing mode comprising delivering first and second LV pacing pulses to the LV using the first and second left ventricular electrodes and, thereafter delivering an RV pacing pulse to the RV using the right ventricular electrode within a single cardiac cycle, wherein the second LV pacing pulse is delivered to a different location in the LV than the first LV pacing pulse.

* * * * *